(12) United States Patent
Masuda

(10) Patent No.: US 11,039,951 B2
(45) Date of Patent: Jun. 22, 2021

(54) ASSISTANCE IMPLEMENT FOR AMELIORATING SLEEP APNEA SYNDROME

(71) Applicant: Souken Co., Ltd., Hiroshima (JP)

(72) Inventor: Hiroto Masuda, Hiroshima (JP)

(73) Assignee: Souken Co., Ltd., Hiroshima (JP)

( * ) Notice: Subject to any disclaimer, the term of this patent is extended or adjusted under 35 U.S.C. 154(b) by 232 days.

(21) Appl. No.: 15/983,691

(22) Filed: May 18, 2018

(65) Prior Publication Data

US 2018/0263809 A1 Sep. 20, 2018

Related U.S. Application Data

(63) Continuation of application No. PCT/JP2016/075777, filed on Sep. 2, 2016.

(30) Foreign Application Priority Data

Dec. 10, 2015 (JP) ................................ 2015-240957

(51) Int. Cl.
*A61F 5/56* (2006.01)

(52) U.S. Cl.
CPC ................ *A61F 5/566* (2013.01); *A61F 5/56* (2013.01)

(58) Field of Classification Search
CPC ...... A61F 5/56; A61F 5/566; A61F 2005/563; A61C 7/08; A61C 7/36; A63B 71/085; A63B 2071/086; A63B 2071/088
See application file for complete search history.

(56) References Cited

U.S. PATENT DOCUMENTS

| | | | |
|---|---|---|---|
| 6,792,942 B1* | 9/2004 | Ho | A61F 5/566 128/200.24 |
| 8,307,823 B2* | 11/2012 | Schmal | A63B 23/18 128/200.24 |
| 2005/0092331 A1* | 5/2005 | D'Agosto | A61F 5/566 128/859 |

FOREIGN PATENT DOCUMENTS

JP 2013106811 6/2013

* cited by examiner

*Primary Examiner* — Ophelia A Hawthorne
*Assistant Examiner* — Camtu T Nguyen
(74) *Attorney, Agent, or Firm* — Potomac Law Group, PLLC; Kenneth Fagin

(57) ABSTRACT

The present disclosure relates to an assistance implement for ameliorating sleep apnea syndrome which is set in an oral cavity of a user to retain an airway of the user. The assistance implement includes: an oral cavity insertion elastic body formed into an arching plate when viewed end-on from the front or rear; and a lip clamping elastic body shaped into a plate, and provided to a front end of the oral cavity insertion elastic body to oppose the oral cavity insertion elastic body from below.

8 Claims, 25 Drawing Sheets

(a)

(b)

CROSS SECTION A-A (a)

(b)

(a)

(b)

CROSS SECTION B-B (a)

(b)

CROSS SECTION C-C

CROSS SECTION D-D

ASSISTANCE IMPLEMENT FOR AMELIORATING SLEEP APNEA SYNDROME

CROSS-REFERENCE TO RELATED APPLICATIONS

This is a continuation of International Application No. PCT/JP2016/075777 filed on Sep. 2, 2016, which claims priority to Japanese Patent Application No. 2015-240957 filed on Dec. 10, 2015. The entire disclosures of these applications are incorporated by reference herein.

BACKGROUND

The present disclosure relates to an assistance implement for ameliorating sleep apnea syndrome.

When a person sleeps in a supine position, the muscles of the whole body relax. In sleep apnea syndrome, the person's tongue root descends because of an influence of the gravity and the tongue blocks his or her airway, causing apnea.

Examples of an assistance implement for ameliorating sleep apnea syndrome include a soft palate stabilizer disclosed in Japanese Unexamined Patent Publication No. 2013-106811. The soft palate stabilizer includes: a holder having a damper protruding backward to make contact with a soft palate and provided in an oral cavity proper, an arch holding the damper and curving along a palate, a pair of jaw passing parts each provided either to a right end or a left end of the arch and housed either in a left retromolar cavity or a right retromolar cavity, and a pair of arms each bending forward at a corresponding one of the jaw passing parts and housed in an oral vestibule; and a reaction plate secured to the arch, curving along a hard palate, and having a front end positioned closer to the front than the jaw passing parts are.

In the disclosure of Japanese Unexamined Patent Publication No. 2013-106811, the entire soft palate stabilizer is held for use in the oral cavity as illustrated in FIGS. 2 and 7 of the publication. Hence, the soft palate stabilizer poses a problem that a user of the soft palate stabilizer might be afraid of accidentally swallowing the soft palate stabilizer.

Moreover, as the publication cites in paragraph and illustrates in FIG. 2, the soft palate stabilizer is held deep into the oral cavity so that a back end of the soft palate stabilizer surrounds a uvula of the soft palate. Thus, when the user puts the soft palate stabilizer in, the soft palate stabilizer causes, for example, faucial reflex, making it difficult for the user to put in the soft palate stabilizer by himself or herself.

Furthermore, as the publication cites in paragraph and illustrates in FIG. 1, the soft palate stabilizer is complex in structure in which a stainless steel core is included in silicone rubber. Such a structure poses a problem of an increase in production costs.

The present disclosure is conceived in view of the above problems and intends to provide an assistance implement for ameliorating sleep apnea syndrome. The assistance implement is easy to insert and provide into an oral cavity, less likely to be accidentally swallowed by the user, significantly simple in structure to decrease production costs of the implement, and capable of securing an airway of the user in sleep.

In the present disclosure, the term "front" related to such terms as front end and forward means the "front" direction of the body of a person in a standing position or in a supine position. The term "back" related to such terms as back end and backward means the "back" direction of the body of a person in a standing position or in a supine position. Hence, for example, when the person is in the standing position, the "back" direction is perpendicular to a direction of the gravity. When the person is in the supine position lying with his or her face upward, the "back" direction corresponds to the direction of the gravity.

SUMMARY

A first aspect of the assistance implement for ameliorating sleep apnea syndrome 1 is made of an elastic body and inserted into a mouth. The assistance implement 1 includes: an oral cavity insertion elastic body 2 formed into a convex arching plate as viewed end-on from the front or the rear of the implement (as if the eyes of the viewer are in the plane of the implement); and a lip clamping elastic body 3 shaped into a plate, and provided to a front end of the oral cavity insertion elastic body 2 to oppose the oral cavity insertion elastic body 2 from below, wherein in a view from below, the lip clamping elastic body 3 is shaped into a substantial rectangle having: a longitudinal length so that the lip clamping elastic body 3 can be clamped between an anterior tooth 11 and a lip 10 and a transverse width so that the lip clamping elastic body 3 can be clamped with the lip 10 in a plan view (i.e., a view looking down on the implement from above), the oral cavity insertion elastic body 2 has: a longitudinal length in which (i) a front end of the oral cavity insertion elastic body 2 is at a front end of the lip clamping elastic body 3 and (ii) a back end of the oral cavity insertion elastic body 2 is close to a soft palate 12; and a transverse width (i) across an area facing the lip clamping elastic body 3 and equal to a transverse width of the lip clamping elastic body 3, and (ii) at a back R behind the facing area and allowing the oral cavity insertion elastic body 2 to make contact with a cheek 20 of an oral cavity bottom 15, the oral cavity insertion elastic body 2 has an area, except an area with which at least a tooth makes contact when a user clicks teeth together, provided with through holes 5, and the facing area forms a tube 4.

A second aspect of the assistance implement 1 according to the first aspect further may further include a protruding portion 32 provided below a transverse center of the oral cavity insertion elastic body 2, and shaped longitudinally elongated from a front end to a back end of the oral cavity insertion elastic body.

A third aspect of the assistance implement 1 according to the second aspect may further include a stopper 30 extending downward from a center back end of the protruding portion 32 and keeping a tongue from sagging, the stopper 30 being shaped into a substantially U-shaped groove, and having a vertical cross-section, opening toward the back R, with respect to a longitudinal direction of the protruding portion 32.

A fourth aspect of the assistance implement 1 according to the third aspect may further include a stopping unit 60 including the protruding portion 32 and the stopper 30, the stopping unit 60 in a first embodiment being integrally formed with the assistance implement of the first aspect, the stopping unit 60 in a second embodiment having a top face of the protruding portion 32 of the stopping unit 60 and a bottom face of the oral cavity insertion elastic body 2 of the assistance implement of the first aspect joined and secured together, or the stopping unit 60 in a third embodiment having the protruding portion 32 of the stopping unit 60 inserted into and secured to: the oral cavity insertion elastic body 2 formed with a stopping unit insertion belt 33 provided below the oral cavity insertion elastic body 2 of the first aspect; and the tube 61 including the stopping unit insertion belt 33.

In a fifth aspect of the assistance implement 1 according to the third aspect, the stopper 30 may include a through hole 31 provided to an outer periphery wall of the stopper 30.

In a sixth aspect of the assistance implement according to the third aspect, the stopper 30 may have a lower portion a surface of which is coated with a coating film 50.

In a seventh aspect of the assistance implement according to the first aspect, the oral cavity insertion elastic body 2 may include: a projecting portion 40 provided to an upper transverse center of the oral cavity insertion elastic body 2 and making contact with a vicinity of the soft palate; and/or a projection 41 making contact with oral mucosa and a tongue.

The assistance implement for ameliorating sleep apnea syndrome 1 in the first aspect is inserted so that the back end of the tube 4 is pressed against the front face of the anterior tooth 11, and the tube 4 is clamped with the lip 10 and the vicinity of the front end of the oral cavity insertion elastic body 2 is bitten with the anterior tooth 11. Hence, the left and right ends of the back end of the oral cavity insertion elastic body 2 make contact with the cheek 20 of the oral cavity bottom 15 such that the assistance implement for ameliorating sleep apnea syndrome 1 is supported at three points in total one of which is the lip 10 and the other two of which are the left and right sides of the cheek 20 of the oral cavity bottom 15. The tube 4 can retain the clearance 9 for inhaling fresh air. In the oral cavity 8, the following effects can be achieved: a vertical clearance can be retained between the top face of the oral cavity insertion elastic body 2 and the hard palate and the soft palate 12, and another vertical clearance can be retained between the bottom face of the oral cavity insertion elastic body 2 and the top face of the tongue. While the user is sleeping in a supine position, such features allow the oral cavity insertion elastic body 2 to reduce the risk of the tongue root 13 sagging, keeping the tongue root 13 from blocking the airway 6 to the lung 18. Hence, sleep apnea syndrome is ameliorated.

When the user does not click his or her teeth together, the upper anterior tooth 11 is positioned forward and the lower anterior tooth 11 is positioned at the back R. Whereas, when the user clicks his or her teeth together, the lower anterior tooth 11 is positioned forward, and so is his or her lower jaw. Hence, lying in a supine position, the user bites the oral cavity insertion elastic body 2 with the anterior tooth 11. As a result, his or her lower jaw is positioned forward, making it easy to retain the airway 6.

The user can finish putting in the assistance implement for ameliorating sleep apnea syndrome 1 by simply curving the oral cavity insertion elastic body 2, and inserting the oral cavity insertion elastic body 2 in, but not into the back of, the oral cavity 8. Hence, the assistance implement for ameliorating sleep apnea syndrome 1 has an advantage that the user can put the assistance implement 1 in very easily without experiencing faucial reflex. In the tube 4, the oral cavity insertion elastic body 2 is maintained in a convex arching shape. Such a feature allows the oral cavity insertion elastic body 2 to easily curve.

In the assistance implement for ameliorating sleep apnea syndrome 1 which is a elastic body, the tube 4 is clamped with the lip 10 while the back end of the tube 4 makes contact in the longitudinal direction with the anterior tooth 11, the left and right ends at the back of the oral cavity insertion elastic body 2 generates a force to bring back from a significantly curved shape to the original shape to produce a reactive force in left and right outward directions, and the oral cavity insertion elastic body 2 makes contact with the cheek 20 of the oral cavity bottom 15 so that the cheek 20 bulges outward. As a result, the assistance implement for ameliorating sleep apnea syndrome 1 is successfully fixed not to be accidentally swallowed by the user, so that the used does not have to worry about swallowing the assistance implement 1.

Salivary glands for salivation include: major salivary glands, such as sublingual glands and submandibular glands, provided around the mouth, the tongue, and the cheek into which the assistance implement for ameliorating sleep apnea syndrome 1 is inserted; and minor salivary glands, also referred to as mucous glands, including labial glands, buccal glands, palatine glands, molar glands, and lingual glands, and dispersed in large number on the oral mucosa. When inserted into the mouth, the assistance implement for ameliorating sleep apnea syndrome 1, which is elastic, slightly changes in shape inside the mouth when the tong and the teeth move. The slight change in shape allows the assistance implement for ameliorating sleep apnea syndrome 1 to stimulate minor salivary glands widely provided in large number on the lip, the cheek 20, and the palate, and facilitate salivation. Such a feature allows the salivation to achieve such advantages as digesting food, keeping oral mucosa from friction and protecting the oral mucosa, keeping teeth from wearing and protecting the teeth, reducing the risk of dental caries and periodontitis by self-cleaning action of the salivation, reducing the growth of bacteria, reducing cognitive decline in taste, and reducing the risk of xerosis in the oral cavity.

Formed of a single kind of material and made of a combination of plates, the assistance implement for ameliorating sleep apnea syndrome 1 is significantly simple in structure. Moreover, the assistance implement for ameliorating sleep apnea syndrome 1 can be formed by integral molding. Such features make it possible to significantly reduce production costs of the assistance implement 1.

When sleep apnea syndrome is relieved, the user can be freed from such problems as snoring, gnashing, throat cold and head cold, head ache and malaise on awakening, excessive drowsiness in the daytime, interrupted sleep at night, lack of sound sleep, and decline in concentration.

Moreover, even though the oral cavity insertion elastic body 2 is inserted into the oral cavity 8, the through holes 5 retain an airway, allowing the user for easy breathing.

The assistance implement for ameliorating sleep apnea syndrome 1 in the second aspect achieves the same advantages as those in the first aspect. In addition, the assistance implement 1 in the second aspect further includes the protruding portion 32 provided to the transverse center of the oral cavity insertion elastic body 2, and shaped longitudinally elongated from the front end to the back end of the oral cavity insertion elastic body 2. Hence, the protruding portion 32 of the oral cavity insertion elastic body 2 becomes hard. Hence, even if the oral cavity insertion elastic body 2 makes contact with the soft palate 12 and the tongue, the oral cavity insertion elastic body 2 is less likely to distort and deform. The oral cavity insertion elastic body 2, which is less likely to distort and deform, can press the tongue so that the tongue does not sag. This feature allows the stopper 30 extending from the protruding portion 32 to facilitate reduction in the risk of the tongue root 13 sagging. Moreover, the bottom face of the protruding portion 32 may be formed slick so that the lower jar tends to be positioned forward.

The assistance implement for ameliorating sleep apnea syndrome 1 in the third aspect achieves the same advantages as those in the second aspect. When the muscle force of the tongue root 13 weakens, the tongue root 13 could block the airway 6 while the user is sleeping in a supine position. The assistance implement 1 in the third aspect further includes the stopper 30 controlling the degree in which the tongue root 13 changes in shape. As a result, the airway is securely retained. Furthermore, the stopper 30 is shaped into a substantially U-shaped tube, and having a vertical cross-section, opening toward the back R, with respect to a longitudinal direction of the protruding portion. Such a feature makes it possible to retain an air flow passage also for the interior of the tube.

Moreover, a study shows that autonomic nerves significantly affect the block of the airway 6 during sleep. Hence, the use of the assistance implement for ameliorating sleep apnea syndrome 1 stimulates the autonomic nerves to control the tongue root 13, thereby further ameliorating sleep apnea syndrome.

The assistance implement for ameliorating sleep apnea syndrome 1 in the fourth aspect achieves an advantage of the first embodiment that involves integrally forming the assistance implement 1 in a short period of time. The assistance implement 1 in the fourth aspect achieves another advantage of the second embodiment that involves using different materials for the oral cavity insertion elastic body 2 and the lip clamping elastic body 3 to be made soft and the protruding portion 32 and the stopper 30 to be made hard, so that the assistance implement 1, which is wider than the mouth of the user, curves for easy insertion into the mouth, and includes a soft portion making contact with the cheek 20; whereas the stopper 30 that is hard stops the tongue from sagging.

Furthermore, the assistance implement for ameliorating sleep apnea syndrome 1 in the forth aspect achieves an advantage of the third embodiment that allows the removable stopper 62, including the protruding portion 32 and the stopper 30, to be removed from the assistance implement 1. Hence, a user whose tongue does not sag much can use the assistance implement 1 with the removable stopper 62 removed therefrom; whereas, a user whose tongue sags much can use the assistance implement 1 with the removable stopper 62 attached thereto. Depending on how much the tongue of the user sags in a supine position, the assistance implement for ameliorating sleep apnea syndrome 1 can be used in an appropriate form.

The assistance implement for ameliorating sleep apnea syndrome 1 in the fifth aspect achieves the same advantages as those in any one of the third to fifth aspects. The assistance implement 1 further includes through holes 31 provided to the stopper 30. Such a feature facilitates a flow of air into the airway 6.

The assistance implement for ameliorating sleep apnea syndrome 1 in the sixth aspect has the stopper 30 a lower portion of which is coated with the coating film 50. Such a feature makes the stopper 30 slick when the lower end makes contact with an inner wall around the pharynx, allowing the user to easily swallow the assistance implement 1.

Moreover, compared with the stopper 30 with no coating film 50 formed, the stopper 30 having the coating film 50 further enlarges the airway because of the thickness of the coating film 50, allowing the user to breathe more easily.

The assistance implement for ameliorating sleep apnea syndrome 1 in the seventh aspect achieves the same advantage as those in any one of the first to sixth aspects. Furthermore, in the assistance implement 1, the oral cavity insertion elastic body 2 has the upper transverse center provided with the projecting portion 40 making contact around the soft palate 13. Such a feature can reliably retain an air flow passage between the soft palate 13 and the tongue.

Moreover, the oral cavity insertion body 2 is provided with a large number of projections 41 making contact with the oral mucosa and the tongue. Such a feature allows the projections 41 to stimulate (i) the oral mucosa to facilitate salivation, and (ii) acupressure points on the tongue for the lever, the kidneys, the spleen, the lungs, and the heart so that these organs function normally.

BRIEF DESCRIPTION OF THE DRAWINGS

In FIG. 25A, the assistance implement for ameliorating sleep apnea in a cross-sectional view taken along line C-C in FIG. 23A has no protruding portion or projection. In FIG. 25B, the assistance implement for ameliorating sleep apnea in a cross-sectional view taken along line D-D in FIG. 23B has a protruding portion and a projecting portion.

DETAILED DESCRIPTION

Figure 10:
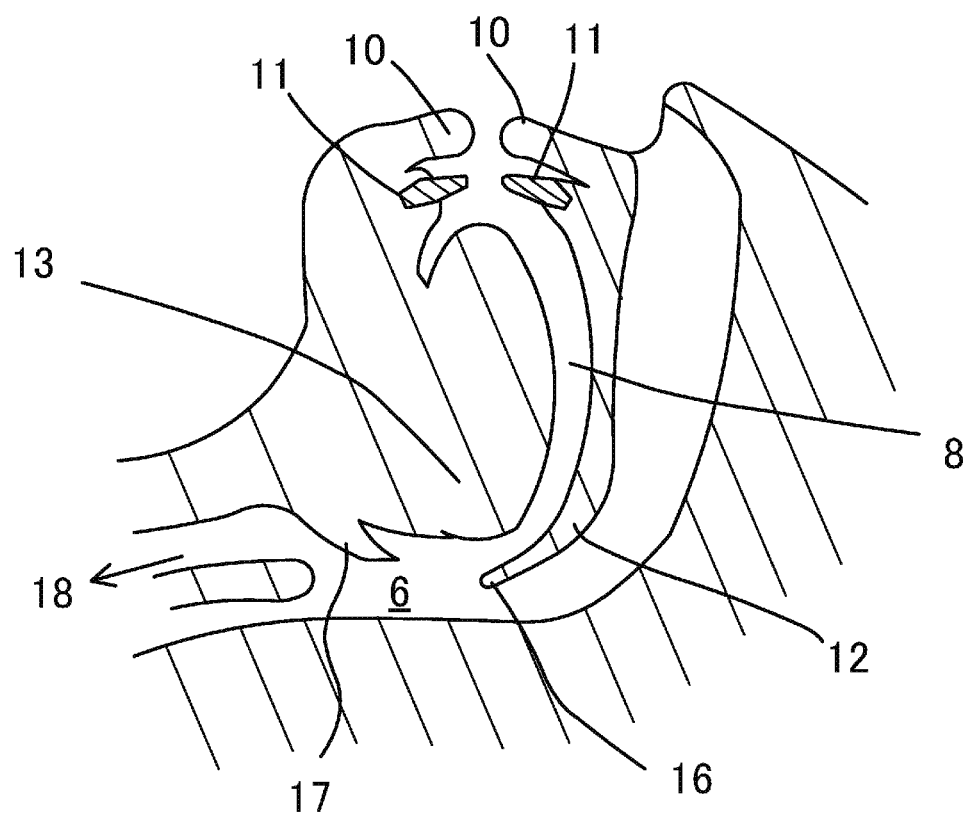
FIG. 10 is a view illustrating the vicinity of the pharynx of a healthy person sleeping in a supine position.
Figure 11:
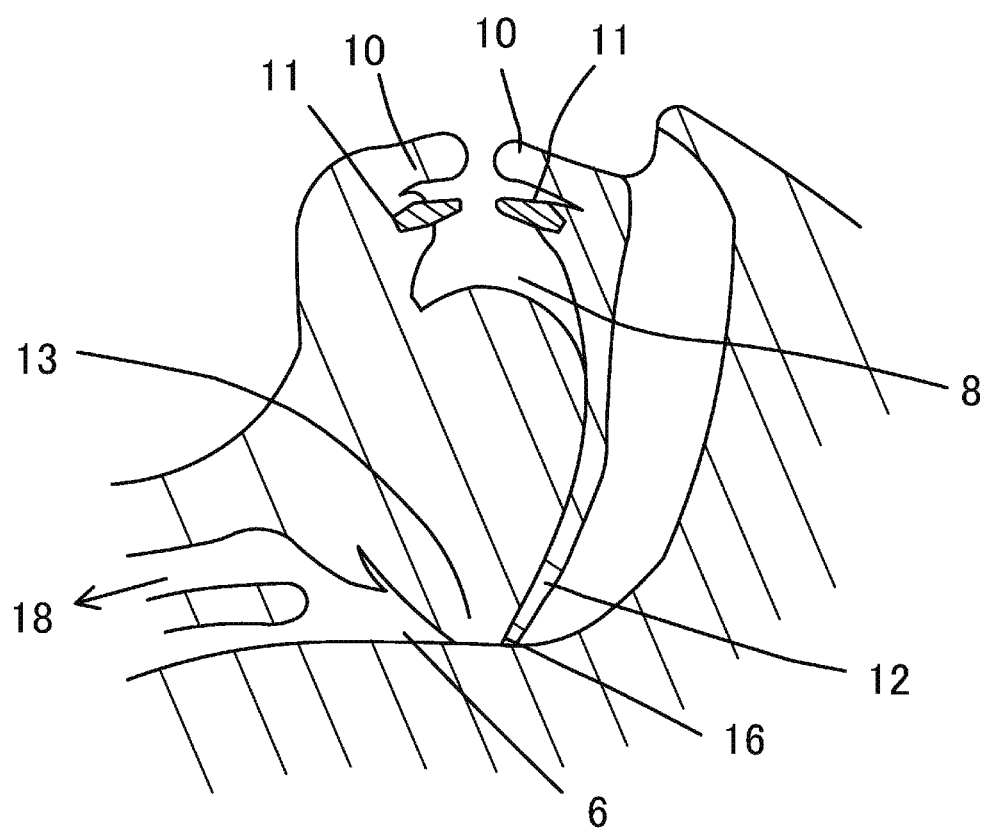
FIG. 11 is a view illustrating the vicinity of the pharynx of a patient of the sleep apnea syndrome sleeping in a supine position.

When people go to bed and fall asleep, the muscles of their whole bodies relax. FIG. 10 shows that when a healthy person sleeps in a supine position and falls asleep, a tongue root 13 in the back of his or her tongue does not either descend downward or block an airway 6 of the pharynx. Meanwhile, in the case of a patient of sleep apnea syndrome as illustrated in FIG. 11, a muscle for changing a position of the tongue root 13 relaxes such that the tongue root 13 sags downward because of an influence of the gravity. As a result, the tongue root 13 blocks the airway 6 of the pharynx. Here, a soft palate 12 and a uvula of soft palate 16 also sag, and block the airway 6 of the pharynx. When the airway 6 is blocked, the air to be sent to a lung 18 is blocked, causing sleep apnea syndrome.

A muscle for changing the position of the tongue is referred to as an extrinsic tongue muscle. The extrinsic tongue muscle includes: a styloglossus muscle pulling the tongue toward the back R; a hyoglossus muscle pulling the tongue downward; a palatoglossus muscle provided to an external rim of the tongue and lifting the tongue dorsum; and a genioglossus muscle projecting the tongue forward. Among these muscles, the styloglossus muscle, the hyoglossus muscle, and the palatoglossus muscle have a significant influence on the tongue root 13 in the back of the tongue. When a person goes to bed and falls asleep, the muscles of the whole body relax, and so do the above-described muscles.

Figure 1:
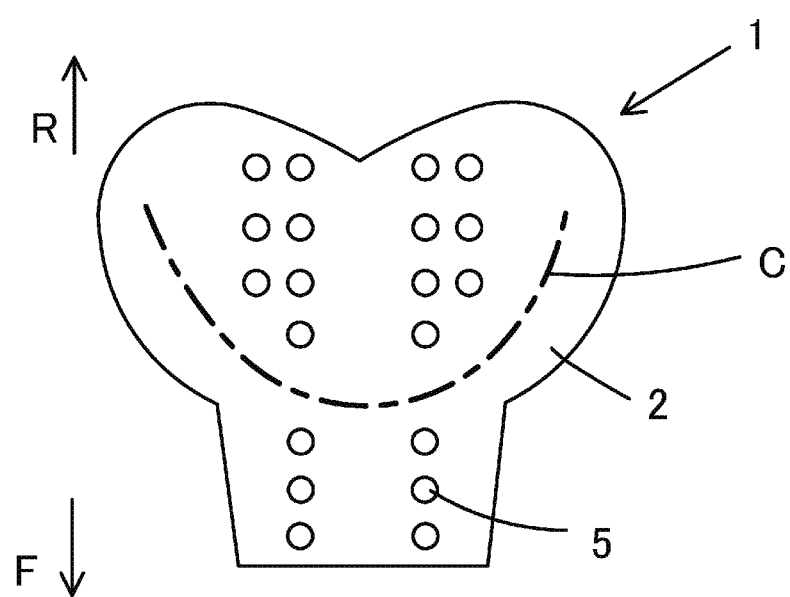
FIG. 1 is a schematic plan view of an assistance implement for ameliorating sleep apnea syndrome according to a first aspect of the present disclosure.
Figure 2:
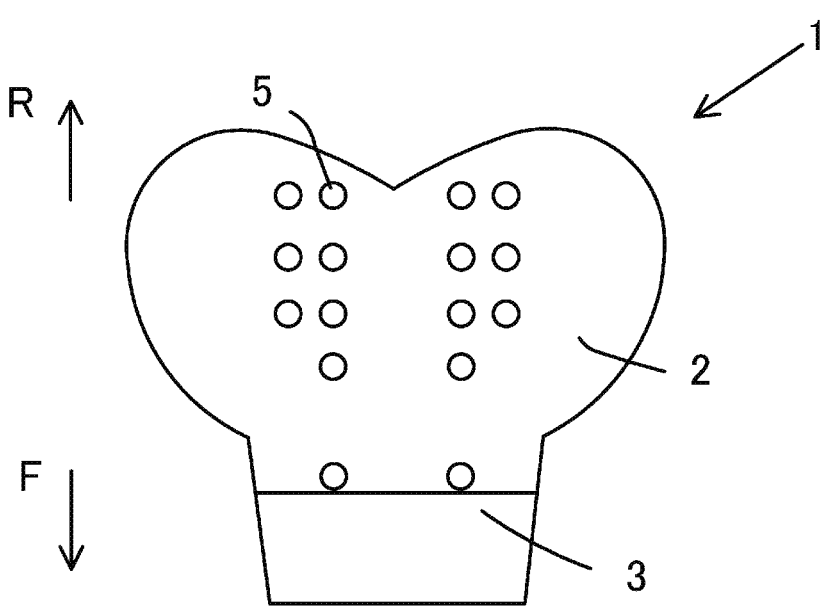
FIG. 2 is a schematic bottom view of the assistance implement for ameliorating sleep apnea syndrome illustrated in FIG. 1.
Figure 3:
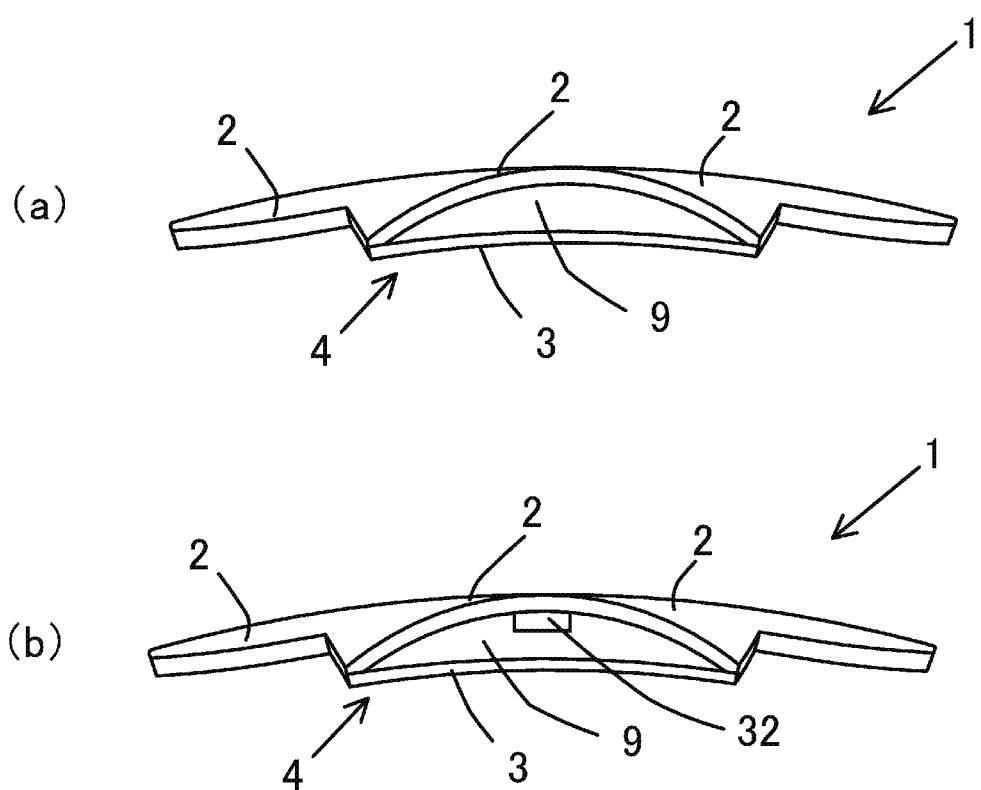
FIG. 3A is a schematic elevation view fend-on from the front) of the assistance implement for ameliorating sleep apnea syndrome in FIG. 1.
FIG. 3B is a schematic elevation view fend-on from the front) of the assistance implement for ameliorating sleep apnea syndrome with a protruding portion.
Figure 8:
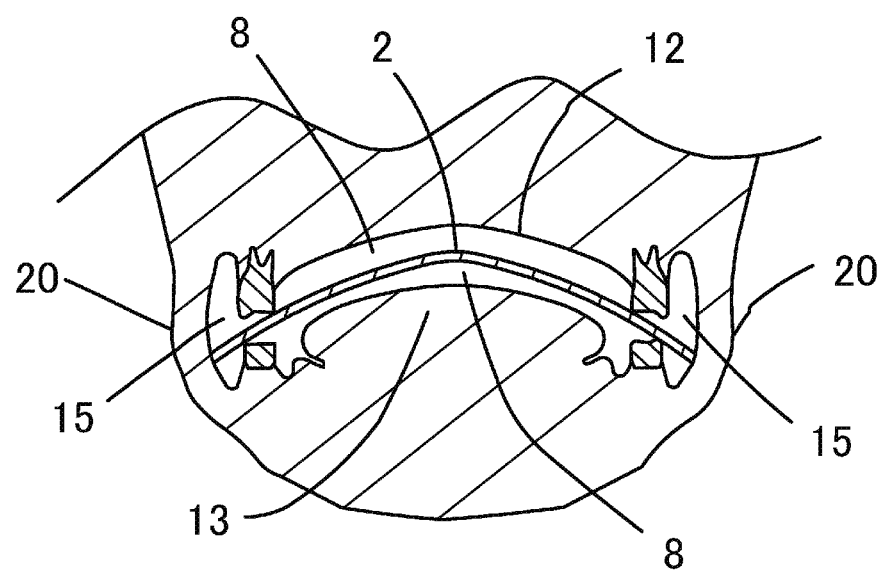
FIG. 8 is a cross-sectional view taken along line A-A of FIG. 6.

As illustrated in FIGS. 1 and 2, an assistance implement for ameliorating sleep apnea syndrome 1 according to the first aspect is made of an elastic body and inserted into a mouth. As illustrated in FIG. 3, the assistance implement 1 includes: an oral cavity insertion elastic body 2 formed into a convex arching plate as viewed end-on from the front of the implement (as if the eyes of the viewer are in the plane of the implement); and a lip clamping elastic body 3 shaped into a plate and provided to a front end of the oral cavity insertion elastic body 2 to oppose the oral cavity insertion elastic body 2 from below. In the bottom view, the lip clamping elastic body 3 is shaped into a substantial rectangle having a longitudinal length so that the lip clamping elastic body 3 can be clamped between an anterior tooth 11 and a lip 10, and a transverse width so that the lip clamping elastic body 3 can be clamped with the lip 10. In the plan view from above, the oral cavity insertion elastic body 2 has a longitudinal length in which (i) a front end of the oral cavity insertion elastic body 2 is at a front end of the lip clamping elastic body 3 as illustrated in the right side view of FIG. 5, and (ii) a back end of the oral cavity insertion elastic body 2 is close to the soft palate 12 and the uvula of soft palate 16 as illustrated in FIG. 6, and a transverse width (i) across an area vertically facing the lip clamping elastic body 3 and equal to a transverse width of the lip clamping elastic body 3, and (ii) at the back R behind the vertically facing area and allowing the oral cavity insertion elastic body 2 to make contact with a cheek 20 of an oral cavity bottom 15 as illustrated in FIG. 8; and the vertically facing area forming a tube 4.

The front end of the oral cavity insertion elastic body 2 forming the tube 4 and the right and left ends of the lip clamping elastic body 3 can be sewn or secured together to constitute the assistance implement for ameliorating sleep apnea syndrome 1. Alternatively, the oral cavity insertion elastic body 2 and the lip clamping elastic body 3 may be integrally molded together to form the assistance implement for ameliorating sleep apnea syndrome 1.

When the assistance implement for ameliorating sleep apnea syndrome 1 is manufactured with a 3D printer or by injection molding, a thickness of the assistance implement for ameliorating sleep apnea syndrome 1 can vary for each given part of the assistance implement 1.

The oral cavity insertion elastic body 2 and the lip clamping elastic body 3 may be made of such flexible elastic bodies as synthetic rubber and a synthetic resin form. Among these elastic bodies, the most suitable one is silicone rubber which is physiologically safe. Moreover, if the oral cavity insertion elastic body 2 and the lip clamping elastic body 3 are excessively thin, it is difficult to press the oral cavity insertion elastic body 2 and the lip clamping elastic body 3 against the cheek 20 of the oral cavity bottom 15, and push the cheek 20 so that the cheek 20 bulges outward, as well as to secure the airway 9 of the tube 4. Meanwhile, if the oral cavity insertion elastic body 2 and the lip clamping elastic body 3 are excessively thick, the elastic bodies 2 and 3 become low in flexibility and high in rubber hardness degree. As a result, it is difficult to easily curve the oral cavity insertion elastic body 2 and the lip clamping elastic body 3, and insert the elastic bodies 2 and 3 into an oral cavity 8. Hence, the oral cavity insertion elastic body 2 and the lip clamping elastic body 3 may have a thickness ranging from 2 mm to 4 mm. Preferably, the oral cavity insertion elastic body 2 and the lip clamping elastic body 3 may have a thickness of approximately 3 mm. The oral cavity insertion elastic body 2 and the lip clamping elastic body 3 of the first aspect preferably contains a material having a rubber hardness degree ranging from 8 to 12.

Figure 5:
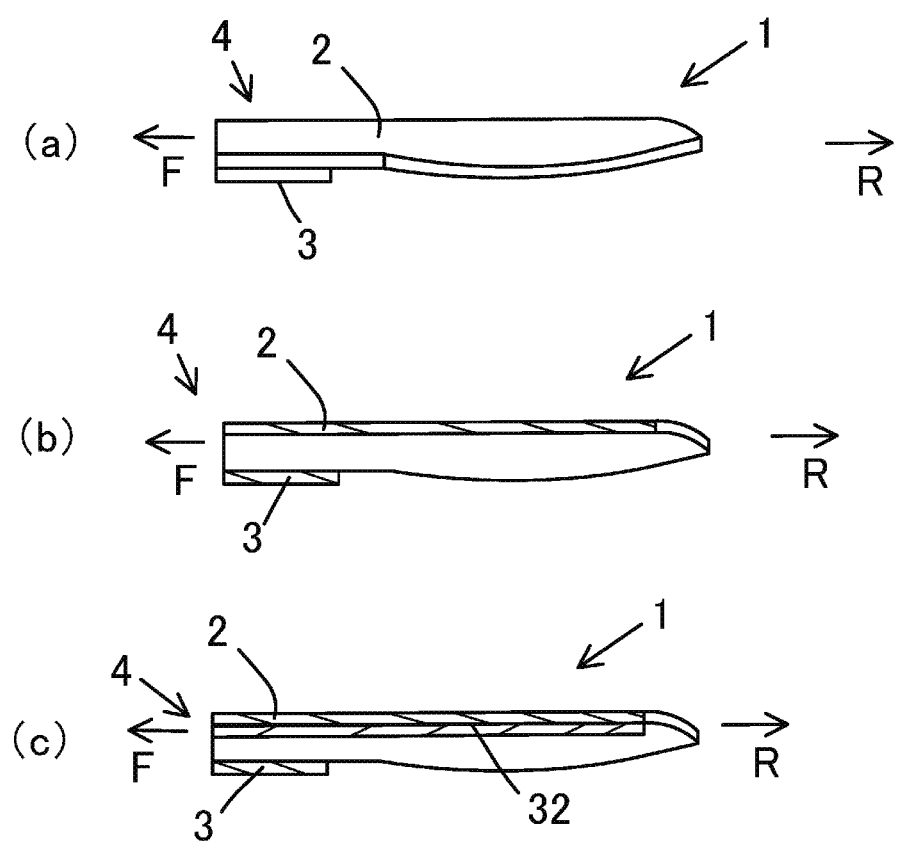
FIG. 5A is a schematic right-side view of the assistance implement for ameliorating sleep apnea syndrome in FIG. 1.
FIG. 5B is a vertical cross-sectional view, in a longitudinal direction, of the assistance implement for ameliorating sleep apnea syndrome in FIG. 5A.
FIG. 5C is a vertical cross-sectional view, in a longitudinal direction, observed from the right side of the assistance implement for ameliorating sleep apnea syndrome having the protruding portion illustrated in FIG. 3B or FIG. 4B.
Figure 6:
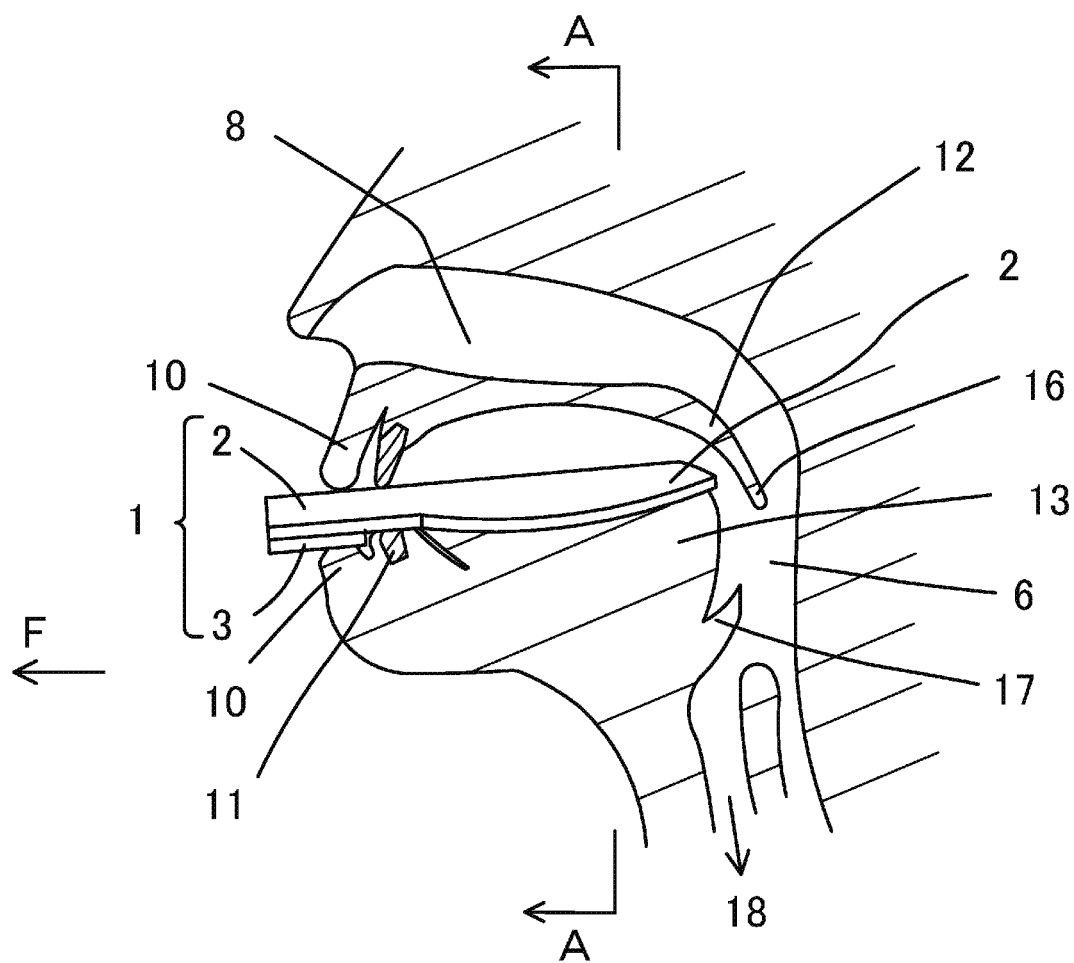
FIG. 6 is a view illustrating an example of how to use the assistance implement for ameliorating sleep apnea syndrome according to the first aspect of the present disclosure.
Figure 7:
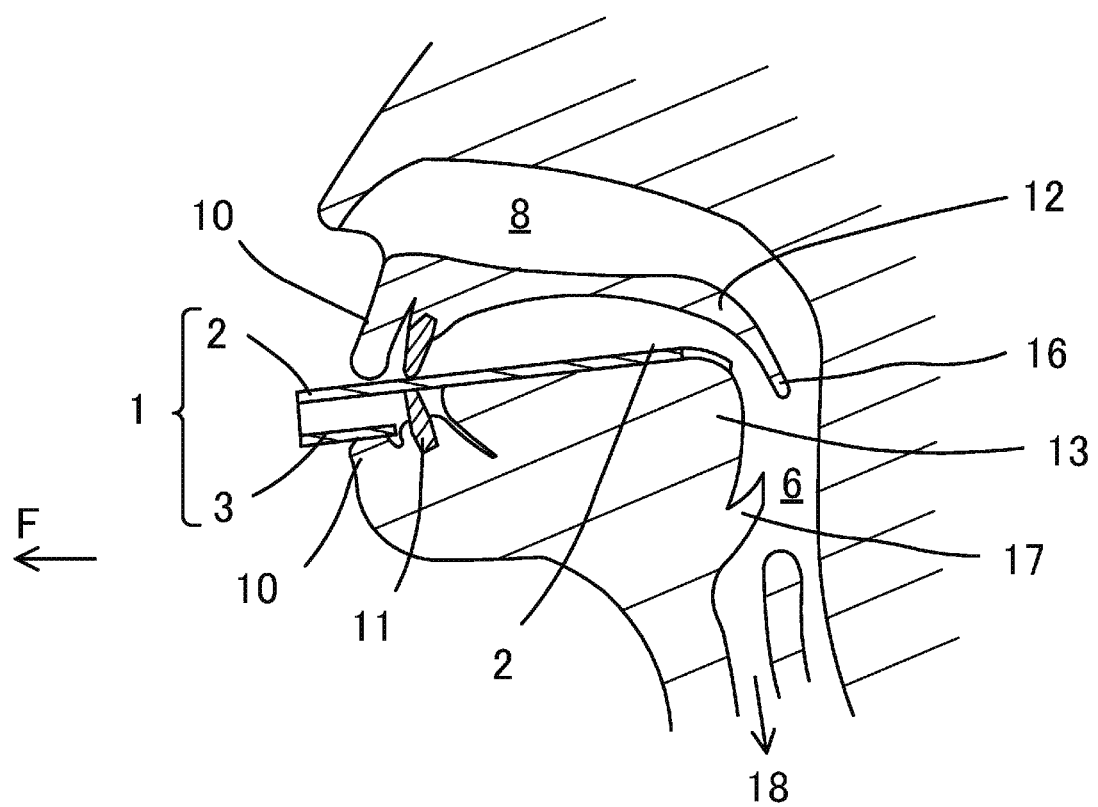
FIG. 7 is a vertical cross-sectional view, in a longitudinal direction, of the transverse center of the assistance implement for ameliorating sleep apnea syndrome in FIG. 6.

As illustrated in FIGS. 2 and 5, the lip clamping elastic body 3 is shaped into a substantially rectangular plate. As illustrated in the planar edge-on view from the side in FIG. 6, the lip clamping elastic body 3 is sized to have a longitudinal length in which the lip clamping elastic body 3 can be clamped between the anterior tooth 11 and the lip 10, and a transverse width in which the lip clamping elastic body 3 can be clamped with the lip 10.

Figure 4:
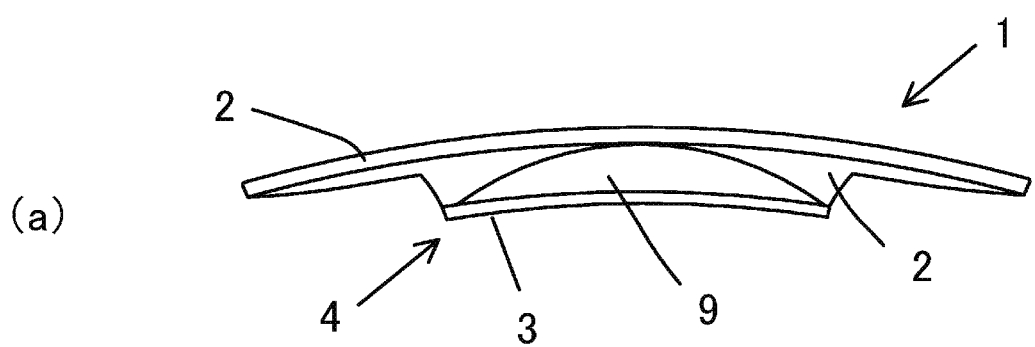
FIG. 4A is a schematic back view of the assistance implement for ameliorating sleep apnea syndrome in FIG. 1.
FIG. 4B is a schematic back view of the assistance implement for ameliorating sleep apnea syndrome with the protruding portion.
Figure 4:
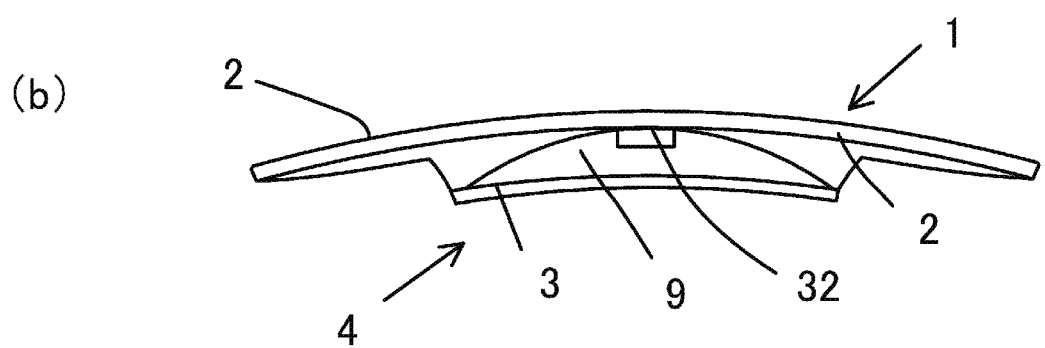
Figure 20:
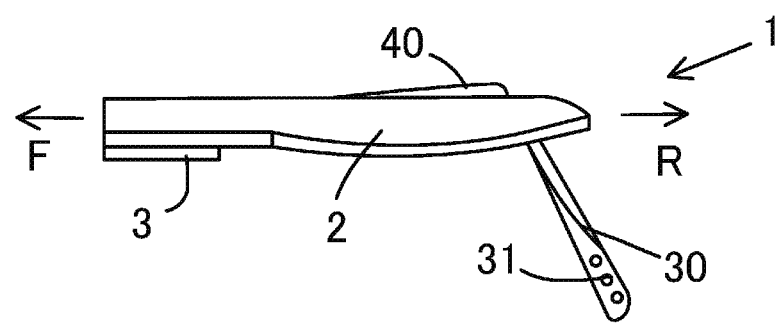
FIG. 20 is a schematic right-side view of the assistance implement for ameliorating sleep apnea syndrome including a projecting portion that is different in shape from the projecting portion in FIG. 18.
Figure 21:
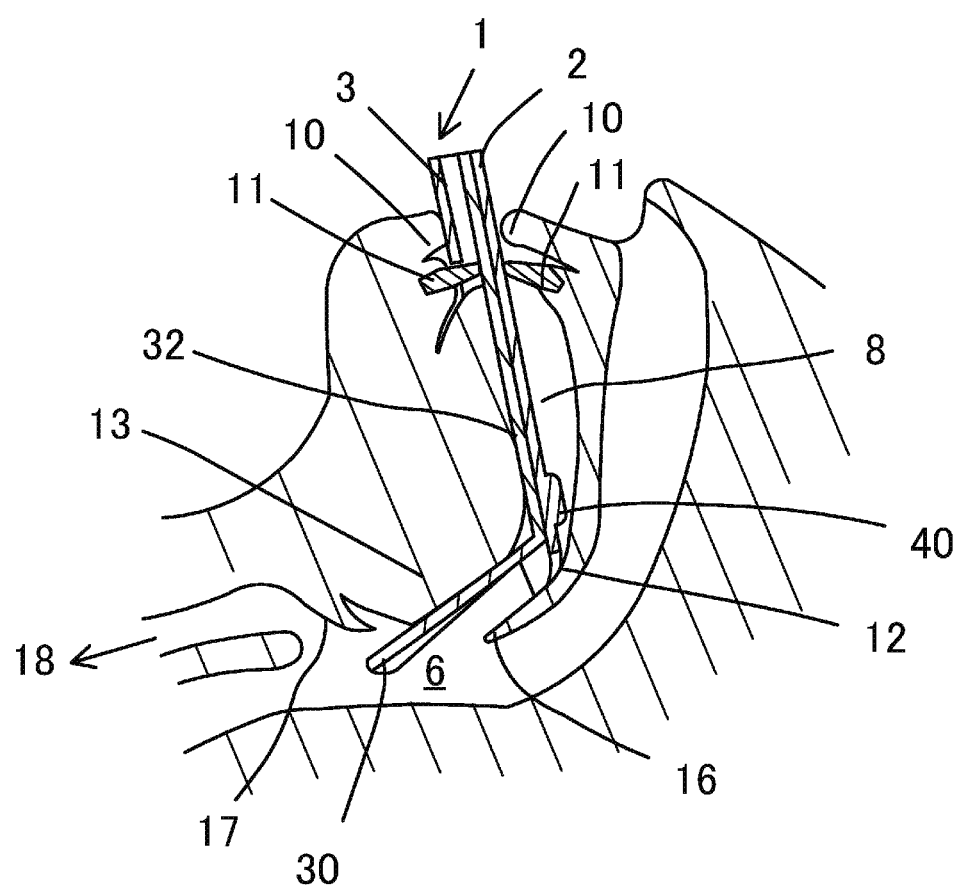
FIG. 21 is a view illustrating an example of how to use the assistance implement for ameliorating sleep apnea syndrome provided with the elongated stopper when the user is in a supine position.

As illustrated in the front views in FIGS. 3A and 3B or in the back views in FIGS. 4A and 4B, the oral cavity insertion elastic body 2 is shaped into a rectangle in the front and a substantial heart in the back. A depression is provided to the center rim of the heart in the back of the oral cavity insertion elastic body 2. As illustrated in FIGS. 20 and 21, the depression is formed so that the assistance implement for ameliorating sleep apnea syndrome 1 is less likely to make contact with the uvula of soft palate 16 of the soft palate 12.

As illustrated in FIG. 6, the oral cavity insertion elastic body 2 is sized to have: a longitudinal length in which (i) the front end is at the front end of the lip clamping elastic body 3 and (ii) the back end is close to the soft palate 12 and the uvula of soft palate 16; and a transverse width (i) across an area facing the lip clamping elastic body 3 and equal to a transverse width of the lip clamping elastic body 3, and (ii) at the back R behind the facing area and capable of making contact with a cheek 20 of an oral cavity bottom 15 as illustrated in FIG. 8. The oral cavity insertion elastic body 2 has a portion positioned at the back R behind the tube 4 and inserted into the oral cavity 8. The portion is plateaued and then curved. An upper back of the portion is positioned close to the soft palate 12 and the uvula of soft palate 16. Left and right ends of the portion make contact with the cheek 20 of the oral cavity bottom 15 so that the cheek 20 bulges outward. Hence, in the plan view from above, the rim of the portion of the back R behind the facing area is desirably curved to be shaped into a substantial heart and a semicircle as illustrated in FIGS. 1 and 2, because the edges of the portion are rounded off, reducing the risk of hurting the interior of the oral cavity 8.

Figure 12:
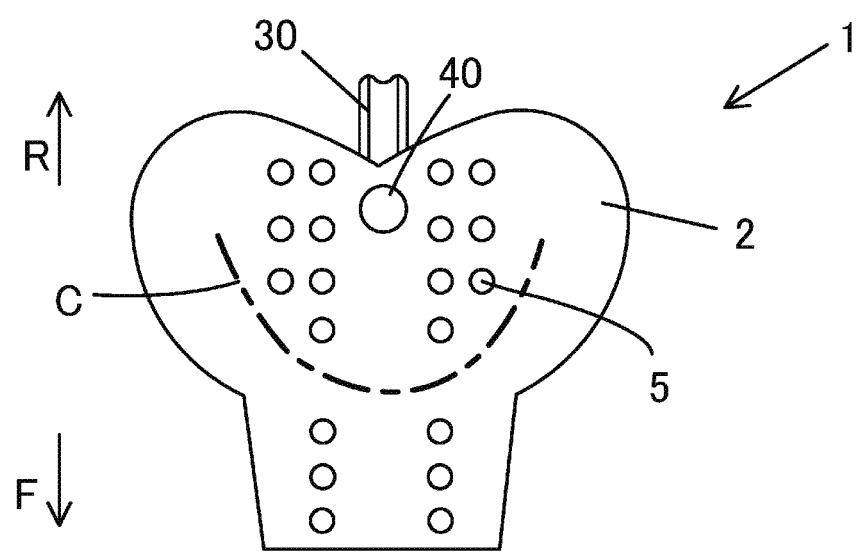
FIG. 12 is a schematic plan view of the assistance implement for ameliorating sleep apnea syndrome provided with a stopper.
Figure 13:
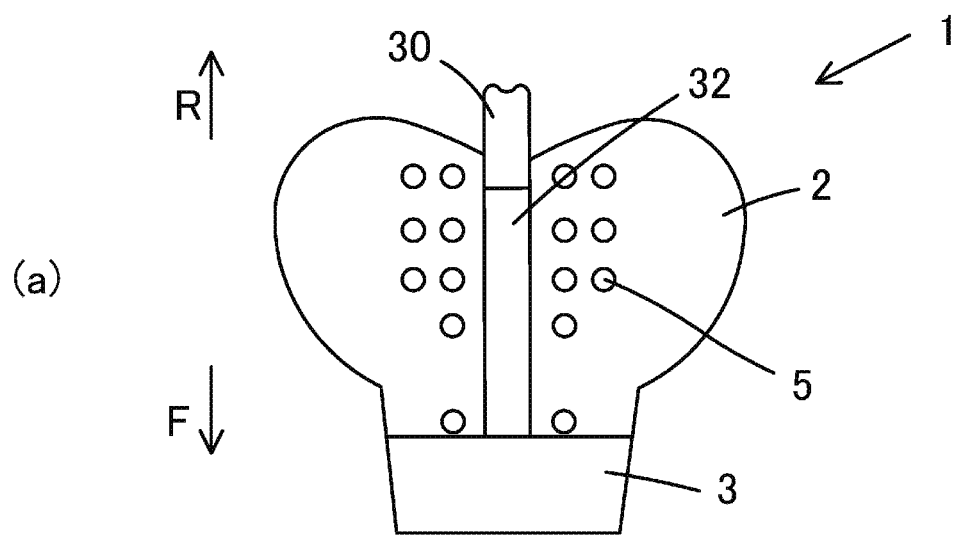
FIG. 13A is a schematic bottom view of the assistance implement for ameliorating sleep apnea syndrome provided with the stopper. The protruding portion of the stopper is integrated with, or secured to, an oral cavity insertion elastic body.
FIG. 13B is a view illustrating how a removable controller, separated from the oral cavity insertion elastic body, is removable.
Figure 13:
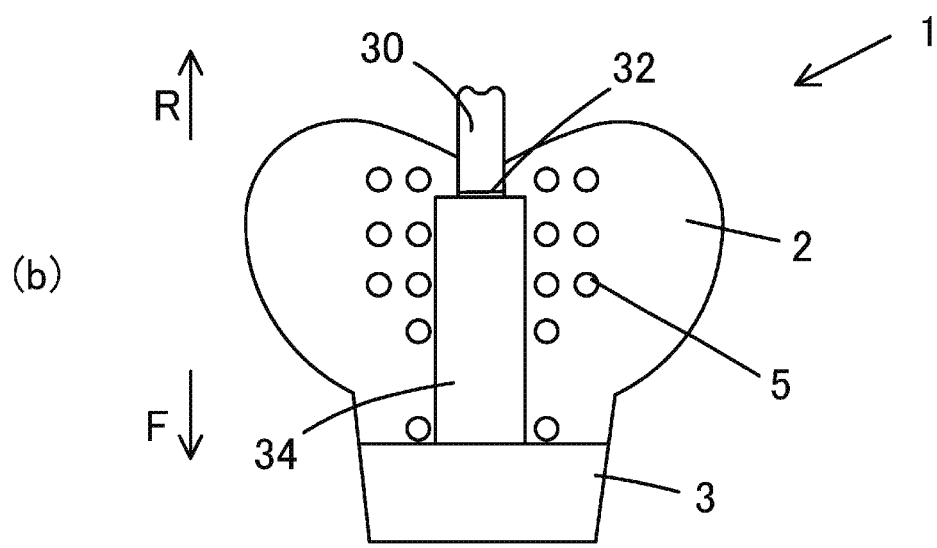
Figure 14:
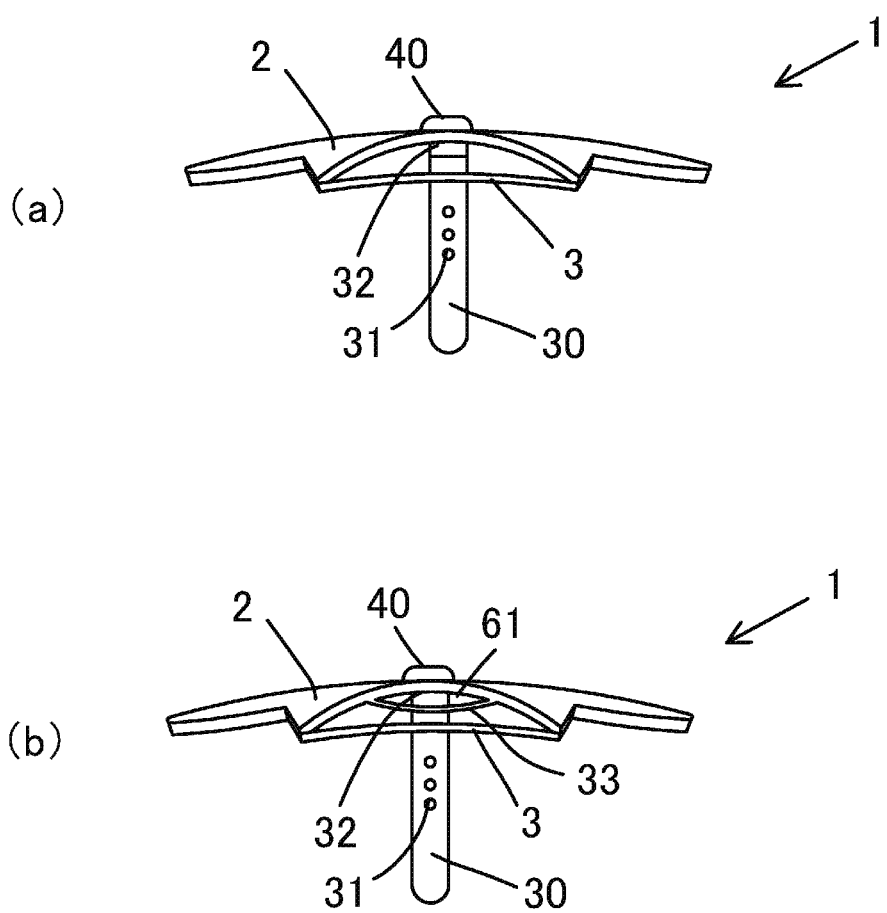
FIG. 14A is a schematic elevation view of the assistance implement for ameliorating sleep apnea syndrome provided with the stopper. The protruding portion of the stopper is integrated with, or secured to, the oral cavity insertion elastic body.
FIG. 14B is a view illustrating how a removable controller, separated from the oral cavity insertion elastic body, is removable.

Moreover, as illustrated in FIG. 1, the oral cavity insertion elastic body 2 has a portion, other than the tube 4, provided with multiple through holes 5. The positions, numbers, and sizes of the through holes 5 may be appropriately determined for each of users to facilitate the breathing of the user. Moreover, the through holes 5 would rather not be provided to the area illustrated with a broken line C in FIG. 1 or FIG. 12; that is, a portion with which teeth such as an anterior tooth and a back tooth make contact, so as to keep the teeth from getting caught in the through holes 5. Then, as illustrated in FIGS. 6 to 9, a space is retained between the curved oral cavity insertion elastic body 2 and the hard palate in the front of the palate, and between the curved oral cavity insertion elastic body 2 and the soft palate 12 in the back of the palate. Moreover, another space is also retained between the curved oral cavity insertion elastic body 2 and the top face of the tongue.

When the assistance implement for ameliorating sleep apnea syndrome 1 presses the left and right cheeks 20 of the oral cavity bottom 15 so that the cheeks 20 bulge outward, and a muscle, connected to the cheeks 20 pulled outward, transversely pulls the extrinsic tongue muscle including the styloglossus muscle, the hyoglossus muscle, and the palatoglossus muscle. Hence, even when the styloglossus muscle, the hyoglossus muscle, and the palatoglossus muscle relax while the user is sleeping in a supine position, the extrinsic tongue muscle is less likely to extend toward the back; that is, in a direction in which the extrinsic tongue muscle blocks the airway 6. Such features allow the tongue root 13 to be less likely to descend toward the back, reducing the risk that the tongue root 13 blocks the airway 6 of the pharynx.

Even if the tongue root 13 should descend toward the back due to the gravity, the curved oral cavity insertion elastic body 2 surrounds the top and both sides of the tongue root 13 as illustrated in FIGS. 6 to 9. Hence, the oral cavity insertion elastic body 2 can reduce the risk of the tongue root 13 descending, keeping the airway 6 from being blocked.

While the user is sleeping, the assistance implement for ameliorating sleep apnea syndrome 1 inserted into the mouth retains a clearance 9 into which air is inhaled from the tube 4 clamped with the lip 10. Inside the oral cavity 8, an air flow passage is retained for a space between the oral cavity insertion elastic body 2 and the tongue, and for a space between the through holes 5 and oral cavity insertion elastic body 2 and the hard palate and the soft palate 12. Such a feature reduces the risk that the tongue root 13 at the pharynx blocks the airway 6.

Figure 9:
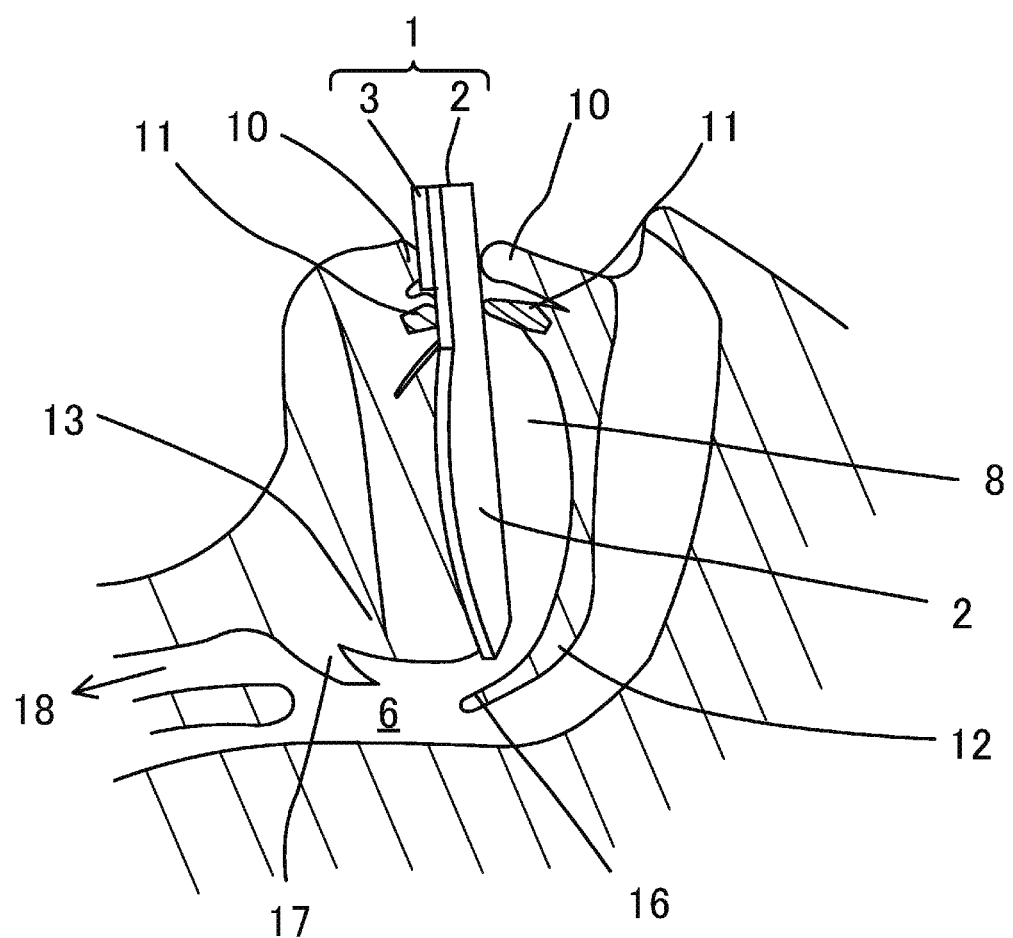
FIG. 9 is a view illustrating an example of how to use the assistance implement for ameliorating sleep apnea syndrome according to the first aspect of the present disclosure when a user is in a supine position.

Hence, in FIG. 9, the air for breathing is inhaled from the lip 10 to the lung 18 in the order of: the clearance 9 of the tube 4, the space between the oral cavity insertion elastic body 2 and the tongue, the through holes 5, the space between the oral cavity insertion elastic body 2 and the hard palate and soft palate 12, the airway 6 at the pharynx, an epiglottis 17 which is open, and the lung 18. Moreover, the airway 6 at the pharynx is not blocked, facilitating breathing through the user's nose. Even though the user is sleeping in a supine position, the above features make it possible to retain the airway 6 from the lip 10 to the lung 18, reducing the risk that the user suffers from sleep apnea syndrome.

When inserted at the mouth, the assistance implement for ameliorating sleep apnea syndrome 1, which is elastic, slightly changes in shape inside the mouth when the tongue and the teeth move. The slight change in shape allows the assistance implement for ameliorating sleep apnea syndrome 1 to stimulate minor salivary glands widely provided in large number on the oral mucosa, facilitating salivation. Hence, even though the user is sleeping in a supine position with his or her mouth open, the above feature makes it possible to maintain humidity in the mouth at an appropriate level, keeping the mouth from drying.

When a back end of the tube 4 makes contact, and interferes in the longitudinal direction, with the anterior tooth 11, and the oral cavity insertion elastic body 2, which is an elastic body, generates a force to bring back from a significantly curved shape to the original shape, the left and right ends of the oral cavity insertion elastic body 2 produces a reactive force in left and right outward directions. The reactive force causes the left and right ends of the oral cavity insertion elastic body 2 to press the cheek 20 of the oral cavity bottom 15 to bulge outward as illustrated in FIG. 8. The pressed cheek 20 produces a reactive force clamping the oral cavity insertion elastic body 2 hard. As a result, the position of the oral cavity insertion elastic body 2 is fixed so that the assistance implement for ameliorating sleep apnea syndrome 1 is successfully kept from being swallowed by the user.

Described next is a protruding portion 32. As illustrated in FIGS. 3B, 4B, 5C, 13, 14, 19, 21, and 22, the protruding portion 32 is provided below the transverse center of the oral cavity insertion elastic body 2, and shaped longitudinally elongated from the front end to the back end of the oral cavity insertion elastic body 2. A cross-section of the protruding portion 32 is shaped into a column such as a rectangular one and a trapezoid one. The protruding portion 32 is used for hardening the transverse center of the oral cavity insertion elastic body 2 made of a soft material. As illustrated in FIG. 9, a hardened longitudinal center of the oral cavity insertion elastic body 2 keeps the oral cavity insertion elastic body 2 from significantly distorting and allows the oral cavity insertion elastic body 2 to press the tongue to retain the airway in the oral cavity 8. As illustrated in FIG. 21, the hardened center allows the stopper 30, extending from the oral cavity insertion elastic body 2, not to give in the reactive force from the tongue root 13 such that the tongue root 13 can be kept from sagging.

The protruding portion 32 formed hardens a longitudinal portion of the transverse center of the assistance implement for ameliorating sleep apnea syndrome 1. If the portion is to be more hardened, the protruding portion 32 will be made of a material harder than that of the oral cavity insertion elastic body 2. For example, when silicone rubber is used, the rubber hardness degree is appropriately set ranging from 8 to 12 when the protruding portion 32 and the oral cavity insertion elastic body 2 are the same in rubber hardness degree. If the protruding portion 32 is to be harder, the rubber hardness degree of the oral cavity insertion elastic body 2 is appropriately set ranging from 3 to 8, and the rubber hardness degree of the protruding portion 32 is appropriately set ranging from 10 to 20.

The oral cavity insertion elastic body 2 of the first aspect may be the same in rubber hardness degree as the protruding portion 32. Alternatively, as illustrated in FIG. 5C, the oral cavity insertion elastic body 2 may be different in rubber hardness degree from the protruding portion 32.

Described next is how the assistance implement for ameliorating sleep apnea syndrome 1 of a third aspect works to keep the airway 6 from being blocked with the tongue root 13 that is likely to sag in a supine position as illustrated in FIGS. 12 to 20, if the muscle force of the tongue root 13 becomes significantly weak. This assistance implement for ameliorating sleep apnea syndrome 1 is provided with the stopper 30 extending downward from the center back end of the protruding portion 32 and keeping the tongue from sagging. As illustrated in FIG. 19E, the stopper 30 is shaped into a substantially U-shaped groove, and having a vertical cross-section, opening toward the back R, with respect to the longitudinal direction of the protruding portion 32.

Figure 22:
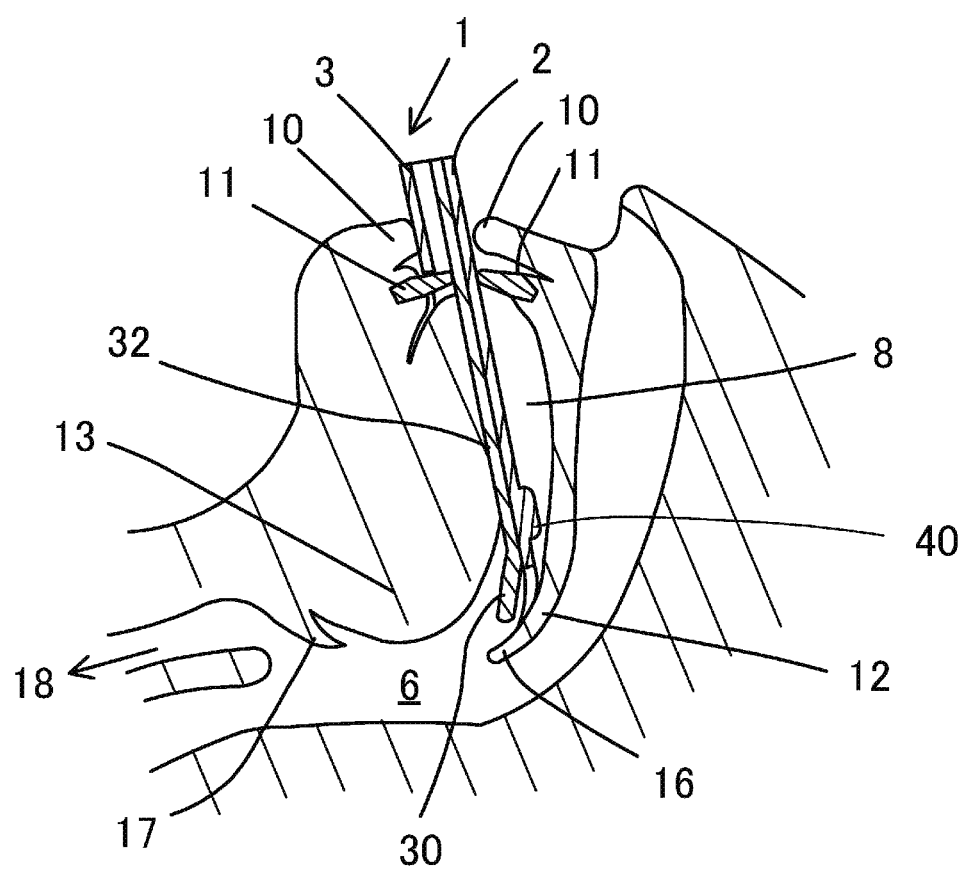
FIG. 22 is a view illustrating an example of how to use the assistance implement for ameliorating sleep apnea syndrome provided with the short stopper when the user is in a supine position.

Described next is the stopper 30. As illustrated in FIGS. 18A, 19A, and 21, the stopper 30 may be bent into a substantial L-shape with respect to the longitudinal direction of the protruding portion 32 and shaped elongated. Alternatively as illustrated in FIGS. 18C, 19D, and 22, the stopper 30 would rather not be bent with respect to the longitudinal direction of the protruding portion 32 and may be shaped short. The stopper 30 bent into the substantial L-shape and shaped elongated is suitable to a symptom in which the tongue root 13 is likely to sag. The stopper 30 not significantly bent and shaped short according to the first aspect is suitable to a symptom in which even though the tongue root 13 sags, the stopper 30 shaped elongated is not required.

Depending on the degree of the tongue root 13 sagging in a supine position, the length and the bending angle of the stopper 30 are set. In the assistance implement for ameliorating sleep apnea syndrome 1 of the first aspect, the stopper 30 for use is (i) shaped short and forms an angle of close to 180° with the protruding portion 32 if the tongue root 13 does not significantly sag, and (ii) shaped elongated and forms an angle of close to 90° with the protruding portion 32 if the sagging tongue root 13 is likely to block the airway 6.

A material determined for the stopper 30 is sufficiently hard so that the stopper 30 is less likely to be deformed by the reactive force from the sagging tongue root 13. Moreover, the angle formed between the protruding portion 32 and the stopper 30 needs to be resistant to deformation by the reactive force from the sagging tongue root 13. Thus, the protruding portion 32 and the stopper 30 may be integrally molded together to easily form the angle. To be easily formed in a single piece with the protruding portion 32, the stopper 30 may be made of the same material as that of protruding portion 32.

As illustrated in FIGS. 21 and 22, the stopper 30 can forcibly and physically stop the tongue root 13 from sagging and blocking the airway 6 even though the user is sleeping in a supine position.

Figure 15:
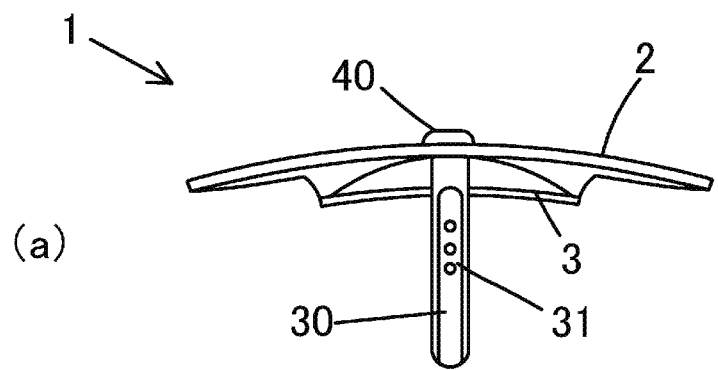
FIG. 15A is a schematic back view of the assistance implement for ameliorating sleep apnea syndrome provided with the stopper. The protruding portion of the stopper is integrated with, or secured to, the oral cavity insertion elastic body.
FIG. 15B is a view illustrating how a removable controller, separated from the oral cavity insertion elastic body, is removable.
Figure 15:
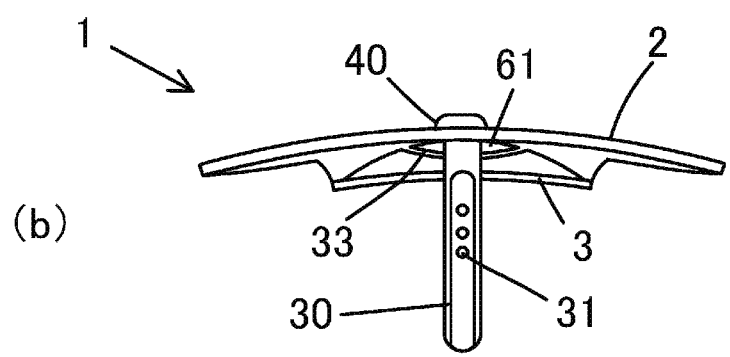
Figure 16:
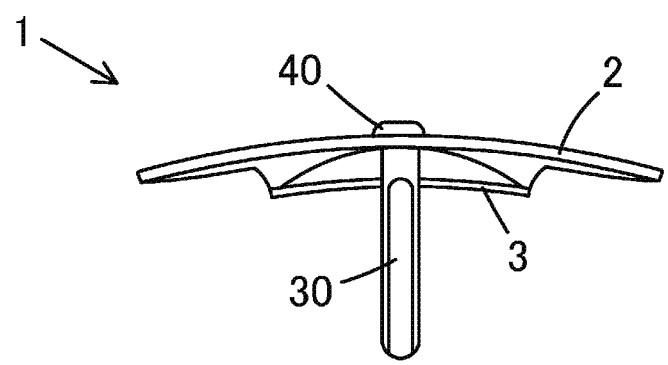
FIG. 16 is a schematic back view of the assistance implement for ameliorating sleep apnea syndrome with no through holes provided to the stopper.
Figure 18:
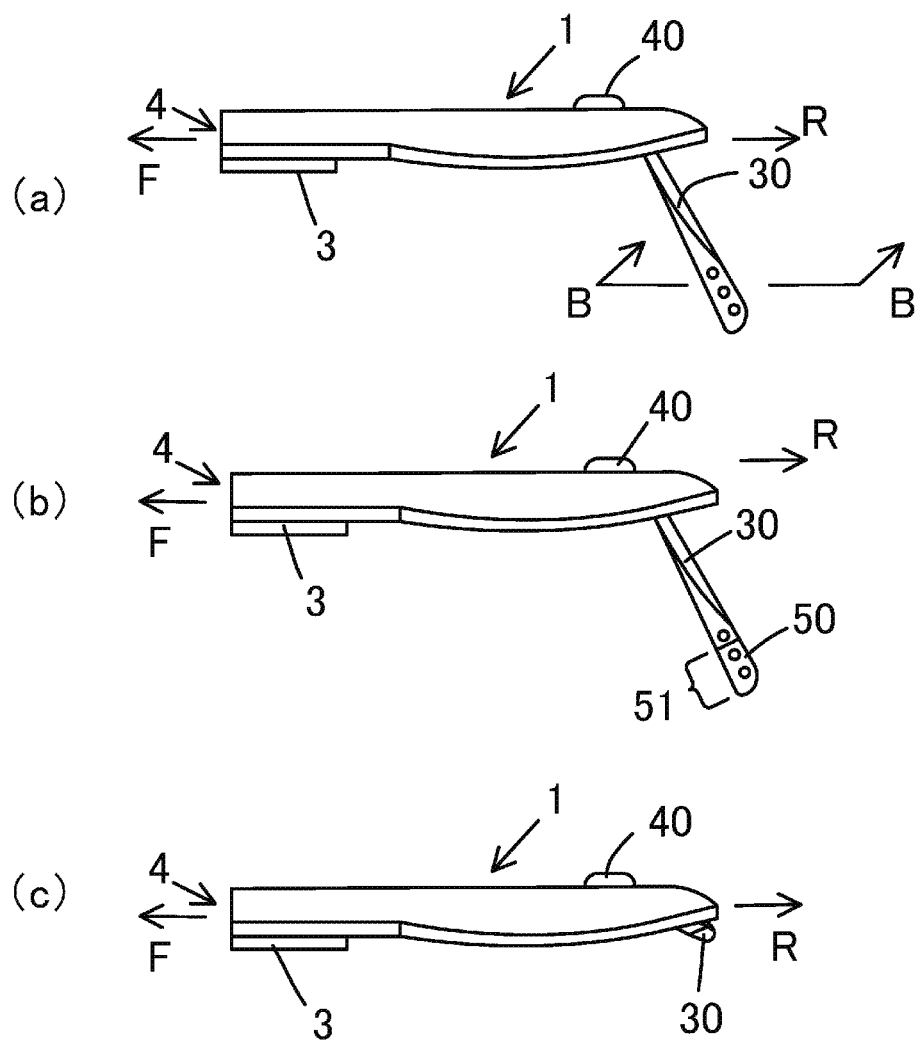
FIG. 18A is a schematic right-side view of the assistance implement for ameliorating sleep apnea syndrome provided with the stopper shaped elongated and bent in a substantial L-shape with respect to the longitudinal direction of the protruding portion
FIG. 18B illustrates the stopper, in FIG. 18A, a lower portion of which is coated with a coating film.
FIG. 18C illustrates the stopper shaped short and slightly bent with respect to the longitudinal direction of the protruding portion.
Figure 19:
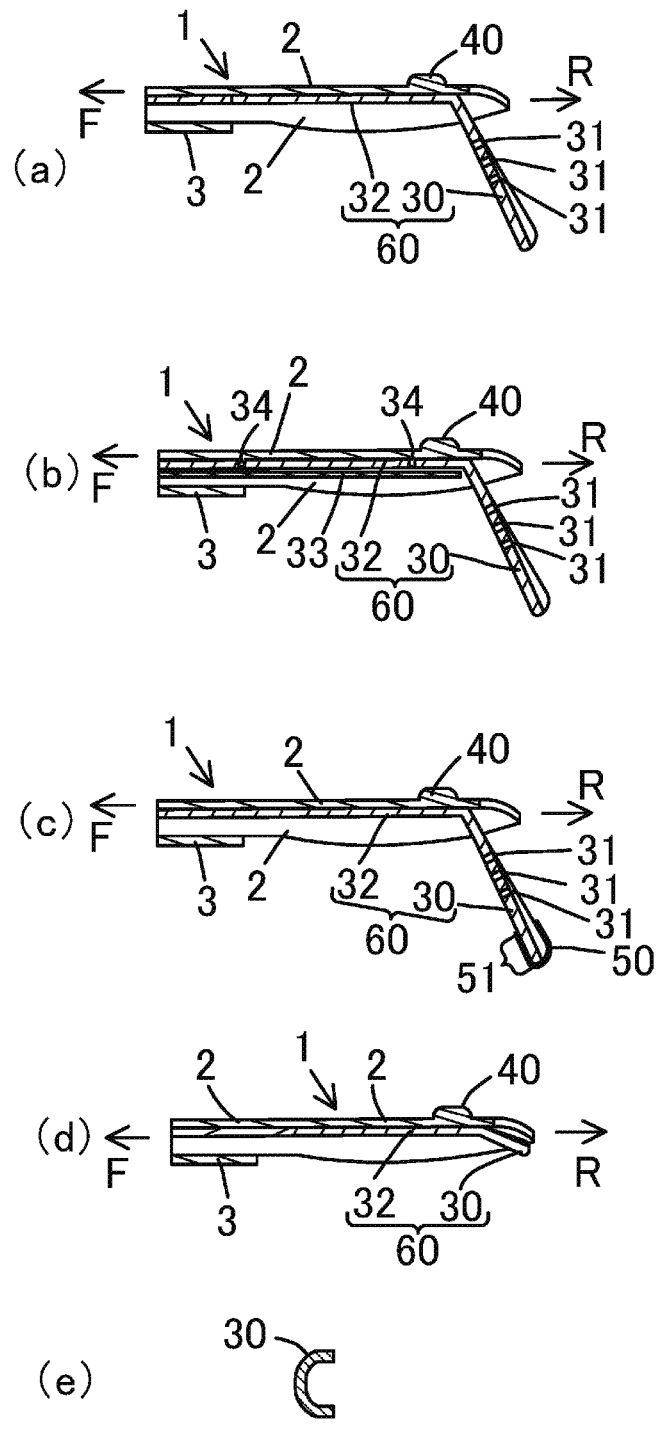
FIG. 19A is a view illustrating the assistance implement for ameliorating sleep apnea syndrome including the stopper. The illustration is a vertical cross-sectional view, in a longitudinal direction, of the transverse center of the assistance implement in FIG. 18A with the protruding portion integrated with, or secured to, the oral cavity insertion elastic body.
FIG. 19B is a view illustrating the assistance implement for ameliorating sleep apnea syndrome including the stopper. The illustration is a vertical cross-sectional view, in a longitudinal direction, of the transverse center of the assistance implement in FIG. 18A when the removable controller can be inserted.
FIG. 19C is a vertical cross-sectional view, in a longitudinal direction, of the transverse center of the assistance implement for ameliorating sleep apnea syndrome in FIG. 18B.
FIG. 19D is a vertical cross-sectional view, in a longitudinal direction, of the transverse center of the assistance implement for ameliorating sleep apnea syndrome in FIG. 18C.
FIG. 19E is a cross-sectional view taken along line B-B of FIG. 18A.

Moreover, as illustrated in FIG. 16, the stopper 30 does not have to have the through holes 31. A portion of the stopper 30 is shaped into a substantial U-shape to retain an air flow passage. As illustrated in FIGS. 15 and 18, the stopper 30 may have the through holes 31 provided to the substantially U-shaped outer periphery wall of the stopper 30. Providing the through holes 31 has an advantage of enlarging the air flow passage.

When the through holes 31 are provided on an upper portion, of the stopper 30, not making contact with the pharynx and tongue, the portion is the center face of the stopper 30 substantially U-shaped as illustrated in FIG. 15. When the through holes 31 are provided on a lower portion, of the stopper 30, making contact with the pharynx and tongue, the portion is a face on each of the left and right sides of the stopper 30 substantially U-shaped as illustrated in FIG. 18. Such features facilitate retention of an airway.

Described next is a material of the assistance implement for ameliorating sleep apnea syndrome 1 including the stopper 30. The stopper 30 and the protruding portion 32 may be integrally molded together so that at least the angle between the stopper 30 and the protruding portion 32 is formed as intended. Hence, the stopper 30 and the protruding portion 32 are made of the same material. The material may be (i) flexible so that the user does not feel a pain on the cheek 20 when the assistance implement for ameliorating sleep apnea syndrome 1 is inserted into the mouth and the left and right ends of the oral cavity insertion elastic body 2 press the cheek 20 outward, and (ii) hard so that the stopper 30 firmly presses the tongue root 13 and keeps the tongue root 13 from sagging.

Hence, depending on a structure such as the size and thickness of each of the parts of the assistance implement for ameliorating sleep apnea syndrome 1, the materials for all the parts of the assistance implement for ameliorating sleep apnea syndrome 1 may be the same. Alternatively, the stopper 30 and the protruding portion 32 alone may be made of a hard material, and the other parts may be made of flexible materials.

For example, when the stopper 30 and the protruding portion 32 alone are made of a hard material (e.g., silicone rubber), the stopper 30 and the protruding portion 32 have a rubber hardness degree ranging from 10 to 20, and the other parts such as the oral cavity insertion elastic body 2 has a rubber hardness degree ranging from 3 to 8.

Moreover, as illustrated in FIGS. 18B and 19C, a surface of a coating area 51 below the stopper 30 is coated with a coating film 50 made of, for example, silicone rubber. Coated with the coating film 50 made of silicone rubber, the lower end of the stopper 30 is likely to be slick when making contact with an inner wall around the pharynx. Such a feature allows the user to easily swallow the assistance implement for ameliorating sleep apnea syndrome 1, and the airway to be easily retained with the thickness of the coating film 50.

An embodiment of the assistance implement for ameliorating sleep apnea syndrome 1 including the stopper 30 may vary, depending on an embodiment of a stopping unit 60 including the protruding portion 32 and the stopper 30 of the assistance implement for ameliorating sleep apnea syndrome 1. In a first embodiment, the stopping unit 60 is integrally formed with the assistance implement for ameliorating sleep apnea syndrome 1 of the first aspect. In a second embodiment, as illustrated in FIG. 19A, a top face of the protruding portion 32 of the stopping unit 60 and a bottom face of the oral cavity insertion elastic body 2 of the assistance implement for ameliorating sleep apnea syndrome 1 of the first aspect are joined and secured together. In a third embodiment, as illustrated in FIG. 19B, the protruding portion 32 of the stopping unit 60 is inserted into and secured to: the oral cavity insertion elastic body 2 formed with the stopping unit insertion belt 33 provided below the oral cavity insertion elastic body 2 of the assistance implement for ameliorating sleep apnea syndrome 1 of the first aspect; and the tube 61 included in the stopping unit insertion belt 33.

In the first embodiment, for example, a body of each of the stopper 30 and the protruding portion 32 is produced first. Then, the bodies are set in a mold for forming the assistance implement for ameliorating sleep apnea syndrome 1 to be integrated into, and produced as, a single piece of the assistance implement 1.

In the second embodiment, for example, a body of each of the stopper 30 and the protruding portion 32 and bodies of other parts such as the oral cavity insertion elastic body 2 are separately manufactured. Then, the bodies are sewn or pasted together so as to be secured together so that the stopping unit 60 is produced.

In the first and second embodiments, when the assistance implement for ameliorating sleep apnea syndrome 1 is manufactured with a 3D printer or by injection molding, a thickness of the assistance implement for ameliorating sleep apnea syndrome 1 can vary for each given part of the assistance implement 1.

In the third embodiment, the stopping unit 60 including the stopper 30 and the protruding portion 32 is removable as a removable stopper 62 from the assistance implement for ameliorating sleep apnea syndrome 1. Hence, the removable stopper 62 can be easily installed in, and removed from, the assistance implement for ameliorating sleep apnea syndrome 1

As illustrated in FIGS. 13B, 14B, 15B, and 19B, in the assistance implement for ameliorating sleep apnea syndrome 1 equipped with the removable stopper 62, the stopping unit insertion belt 33 provided on the bottom face of the oral cavity insertion elastic body 2 forms the tube 61 including the oral cavity insertion elastic body 2 and the stopping unit insertion belt 33. The removable stopper 62 is inserted into the tube 61.

Figure 17:
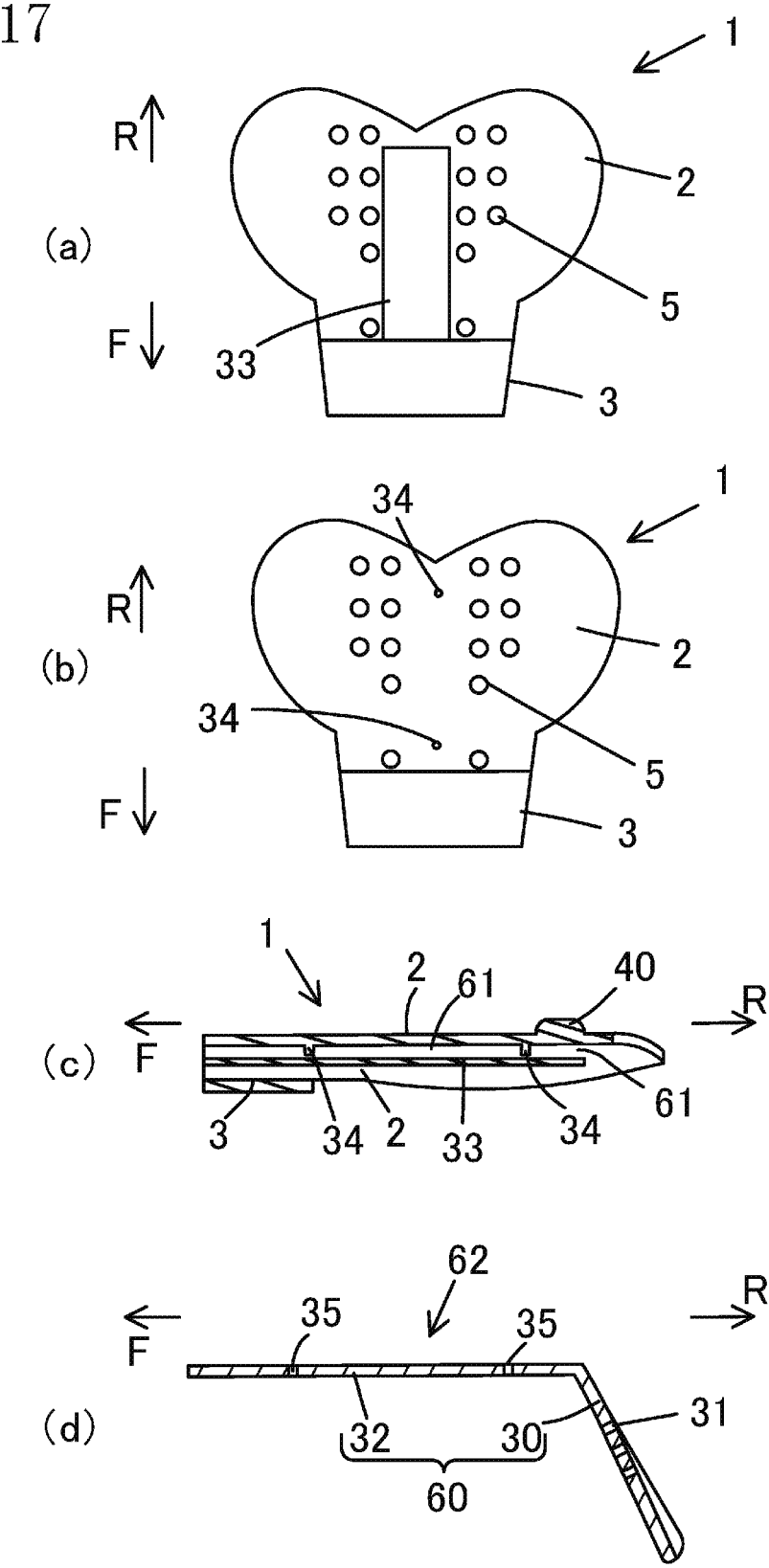
FIG. 17A is a view illustrating a component of the assistance implement for ameliorating sleep apnea syndrome including the removable controller. The view is a schematic bottom view of the assistance implement for ameliorating sleep apnea syndrome with the removable controller removed from the assistance implement.
FIG. 17B is a schematic bottom view of the assistance implement for ameliorating sleep apnea syndrome with a stopping unit insertion belt removed from the assistance implement in the schematic bottom view of FIG. 17A.
FIG. 17C is a schematic right-side view of a cross-section of the longitudinal center of the assistance implement for ameliorating sleep apnea syndrome with the removable controller removed.
FIG. 17D is a schematic right-side view of a cross-section of the longitudinal center of the removable controller.

FIG. 17 shows structures of the removable stopper 62 and the assistance implement for ameliorating sleep apnea syndrome 1 with the removable stopper 62 removed. First, in the structure of the assistance implement for ameliorating sleep apnea syndrome 1 with the removable stopper 62 removed, the stopping unit insertion belt 33 is provided to the center of the assistance implement 1 as illustrated in the bottom view in FIG. 17A, and the tube 61 is formed as illustrated in FIG. 17C. Then, as illustrated in the bottom view of the assistance implement 1 in FIGS. 17B and 17C with the stopping unit insertion belt 33 removed, the projections 34 are provided at multiple places on the bottom face of the oral cavity insertion elastic body 2. Moreover, as illustrated in FIG. 17D, the protruding portion 32 of the removable stopper 62 has holes 35. The projections 34 are fitted into the holes 35.

The removable stopper 62 is installed as follows. First, the left and right sides of the assistance implement for ameliorating sleep apnea syndrome 1 are significantly curved so that the center of the assistance implement 1 rises, such that the tube 61 formed of the bottom face of the oral cavity insertion elastic body 2 and the top face of the stopping unit insertion belt 33 is enlarged. The protruding portion 32 of the stopping unit insertion belt 62 is inserted into this enlarged tube 61. Then, the projections 34 protruding toward the bottom face of the oral cavity insertion elastic body 2 are fitted into the holes 35 of the protruding portion 32. Hence, the removable stopper 62 is installed in the assistance implement for ameliorating sleep apnea syndrome 1. When the removable stopper 62 is removed from the assistance implement for ameliorating sleep apnea syndrome 1, the projections 34 may be pulled out of the holes 35 and the removable stopper 62 may be removed from the tube 61.

Described next is a projecting portion 40. As illustrated in FIG. 18, the projecting portion 40 protrudes at the transverse center, and near the back end to the top, of the oral cavity insertion elastic body 2. If no projecting portion 40 were provided, there would be the risk of narrowing the air flow passage when the oral cavity insertion elastic body 2 makes contact with the soft palate 12. However, providing the projecting portion 40 can reliably retain the air flow passage between the oral cavity insertion elastic body 2 and the soft palate 13. The projecting portion 40 is integrally formed with the oral cavity insertion elastic body 2.

The projecting portion 40 may be formed into any given shape as long as the projecting portion 40 reliably retains an air flow passage between the oral cavity insertion elastic body 2 and the soft palate 13. For example, as illustrated in FIG. 20, the projecting portion 40 may be shaped to have a gentle slope.

Figure 25:
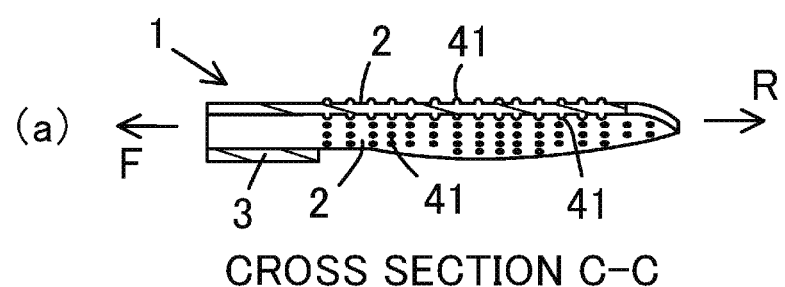
FIG. 25A is a schematic vertical cross-sectional view illustrating projections making contact with oral mucosa and a tongue.
FIG. 25B is a schematic vertical cross-sectional view illustrating projections making contact with oral mucosa and a tongue.
Figure 25:
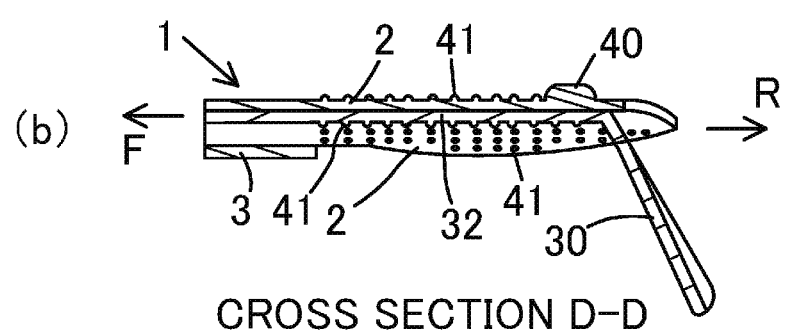

Described next are projections 41 making contact with the oral mucosa and the tongue. As illustrated in FIGS. 25A and 25B, the projections 41 may be formed in any give shape as long as tip ends of the projections 41 are tapered with respect to the bottoms of the projections 41. A cross-section of each of the projections 41 may have any given shape, such as a circular, oval, triangular, rectangular, and pentagonal one. This is because, when making contact with the oral mucosa and the tongue, the tapered tip ends stimulate the oral mucosa and the tongue.

Figure 23:
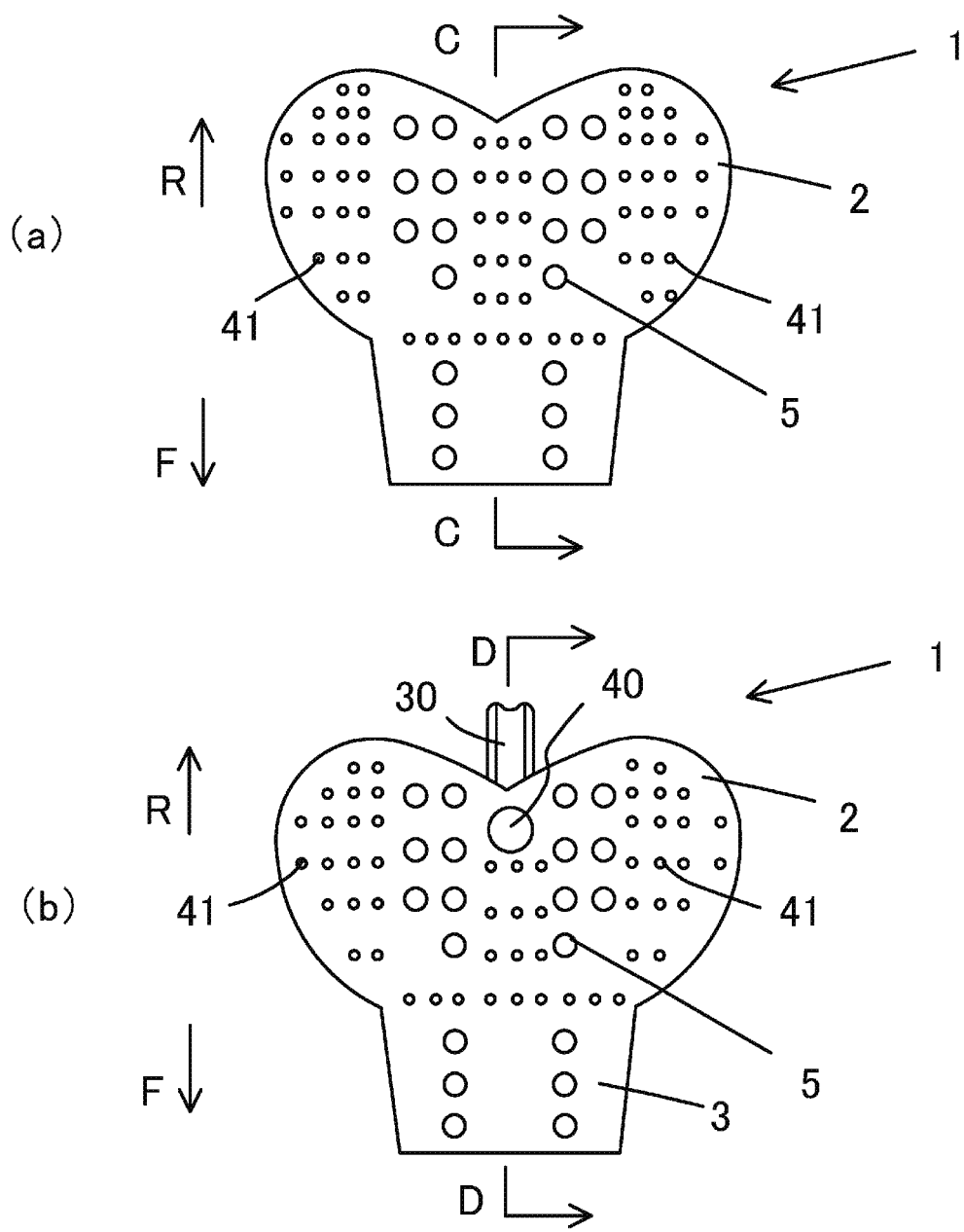
FIG. 23A is a plan view of the assistance implement for ameliorating sleep apnea syndrome having a projection making contact with oral mucosa and a tongue. The plan view illustrates the assistance implement provided with a projection but not with the projecting portion.
FIG. 23B is a plan view of the assistance implement for ameliorating sleep apnea syndrome provided with the projecting portion and the projection.
Figure 24:
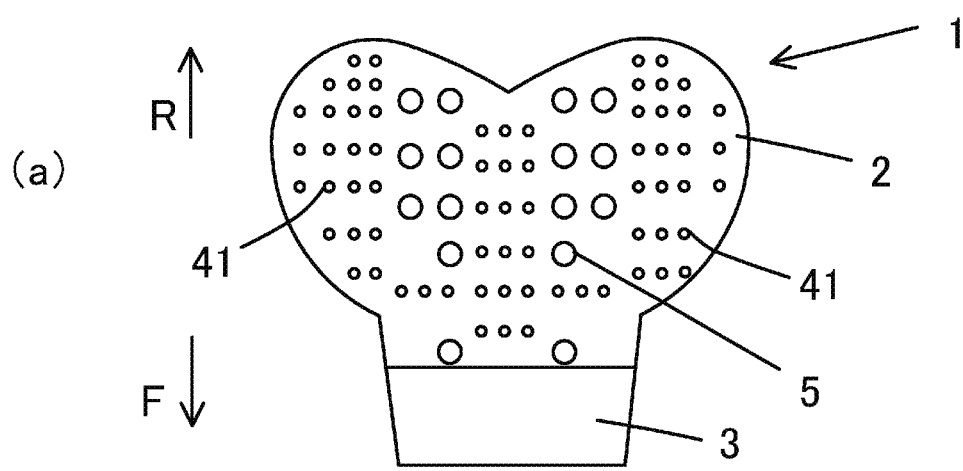
FIG. 24A is a bottom view of the assistance implement for ameliorating sleep apnea syndrome having a protrusion making contact with oral mucosa and a tongue. The bottom view illustrates the assistance implement provided with the projection but not with the protruding portion.
FIG. 24B is a bottom view of the assistance implement for ameliorating sleep apnea syndrome provided with the protruding portion and the projection.
Figure 24:
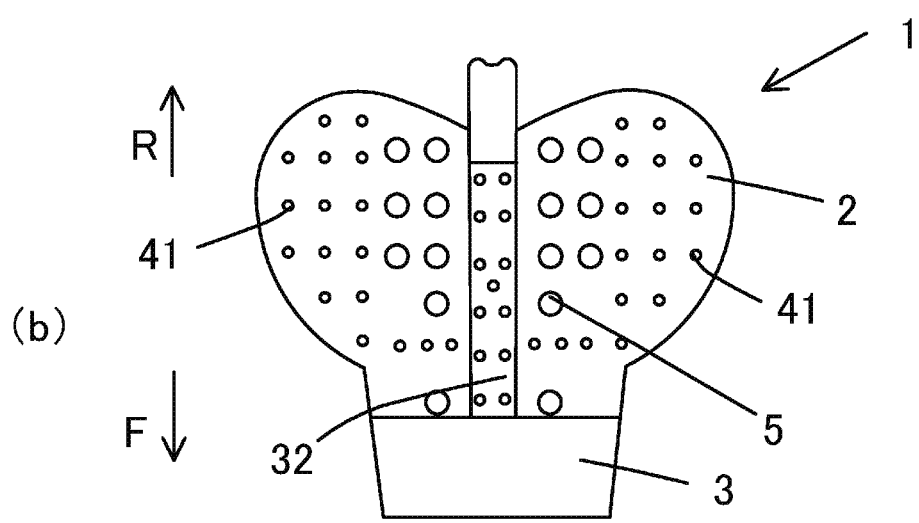

In a plan view from above, the oral cavity insertion elastic body 2 is provided with either (i) the projections 41 but not projecting portion 40 as illustrated in FIG. 23A, or (ii) the projecting portion 40 and the projections 41 as illustrated in FIG. 23B. In either case, many projections 41 are provided to the top face of the oral cavity insertion elastic body 2. Moreover, in a bottom view, the oral cavity insertion elastic body 2 is provided with (i) the projections 41 but not the protruding portion 32 as illustrated in FIG. 24A, (ii) the protruding portion 32 and the projections 41 as illustrated in FIG. 24B, or (iii) the stopping unit insertion belt 33 and the projections 41 which are not shown. In any given case, many projections 41 are provided to, for example, the bottom face of the oral cavity insertion elastic body 2.

The projections 41 make contact with the oral mucosa and stimulate the minor salivary glands to promote salivation, and with the tongue and stimulate acupressure points on the tongue for the lever, the heart, the spleen, the kidneys, and the lungs so that these organs function normally.

Described next is an example of how to use the assistance implement for ameliorating sleep apnea syndrome 1. In the example, the assistance implement for ameliorating sleep apnea syndrome 1 is made of a silicone rubber plate having a thickness of 3 mm. The lip clamping elastic body 3 is sized to have a width of approximately 40 mm, and a longitudinal length of approximately 20 mm. As a whole, the oral cavity insertion elastic body 2 has the largest width of approximately 90 mm and the greatest longitudinal length of 80 mm as seen in a plan view from above. The protruding portion 32 has a width of approximately 20 mm, and a length of approximately 70 mm. The stopper 30 and the protruding portion 32 form an angle of approximately 120°. The stopper 30 has a cross-section, perpendicular to the longitudinal direction, shaped into a substantial U-shape. The stopper 30 has a width of approximately 20 mm, and a length approximately ranging from 45 mm to 50 mm. Moreover, the stopper 30 and the protruding portion 32 alone have a rubber hardness degree of 15. The other parts, such as the oral cavity insertion elastic body 2, have a rubber hardness degree of 5. The sizes of the assistance implement 1 and its parts may be appropriately set, depending on each user.

First, as illustrated in FIGS. 8 and 21, the oral cavity insertion elastic body 2 of the assistance implement for ameliorating sleep apnea syndrome 1 is significantly curved and inserted into the oral cavity 8. When the oral cavity insertion elastic body 2 is inserted, the right-side face thereof in FIGS. 1 and 12 faces the left of the user and the left-side face thereof in FIGS. 1 and 12 faces the right of the user. Then, when the lip clamping elastic body 3 is inserted until the back end thereof reaches the front of the anterior tooth 11, the user stops the insertion and clamps the tube 4 with the lip 10. The user maintains this state and sleeps in a supine position as illustrated in FIG. 9 or FIG. 21. Even though the user sleeps in a supine position, the air flow passage in the following order can be retained: the tube 4, the space between the oral cavity insertion elastic body 2 and the tongue, the through holes 5 of the oral cavity insertion elastic body 2, the space between the oral cavity insertion elastic body 2 and the soft palate 12, the pharynx, the epiglottis 17, and the lung 18. Moreover, an air flow passage from the nose can also be retained. Hence, the airway 6 at the pharynx is not blocked such that sleep apnea syndrome is ameliorated.

Note that the assistance implement for ameliorating sleep apnea syndrome 1 of the first aspect may be used upside down. In this case, the convex protrusion of the curved oral cavity insertion elastic body 2 presses the tongue hard, keeping the tongue root 13 from sagging toward the throat and ameliorating the sleep apnea syndrome.

The assistance implement for ameliorating sleep apnea syndrome 1 including the stopper 30, of the third aspect, illustrated in FIGS. 12 to 22 cannot be used upside down. In this case, as illustrated in FIG. 21, the stopper 30 can reliably reduce the risk that the tongue root 13, which is likely to relax because of the reduction in muscle force, sags and blocks the airway of the pharynx.

What is claimed is:
1. An assistance implement for ameliorating sleep apnea syndrome, made of an elastic body and configured to be inserted into the mouth of a human user, the assistance implement comprising:
  an oral cavity insertion elastic body formed into a convex arching plate as seen in an end-on view of the assistance implement; and a lip clamping elastic body shaped into a plate and provided at a front end of the oral cavity insertion elastic body to oppose the oral cavity insertion elastic body from below, wherein as seen from below, the lip clamping elastic body is shaped into a substantial rectangle having: 1) a longitudinal length that permits the lip clamping elastic body to be held between the user's lips with the lip clamping elastic body abutting the user's lower anterior teeth and extending forwardly past the user's lips when the assistance implement is inserted into the user's mouth; and 2) a transverse width that permits the lip clamping elastic body to be held between the user's lips when the assistance implement is inserted into the user's mouth, as seen from above, the oral cavity insertion elastic body has 1) a longitudinal length in which (i) a front end of the oral cavity insertion elastic body is aligned with a front end of the lip clamping elastic body and (ii) which permits a back end of the oral cavity insertion elastic body to be located close to the user's soft palate when the assistance implement is inserted into the user's mouth; and 2) (i) a first transverse width at a forward region of the oral cavity insertion elastic body, where the lip clamping elastic body is located, that is equal to the transverse width of the lip clamping elastic body, and (ii) a second transverse width behind the forward region that permits the oral cavity insertion elastic body to make contact with the user's cheeks in the region of the user's oral cavity bottom, the oral cavity insertion elastic body has through holes, except in regions with which the user's anterior and posterior teeth will make contact when the assistance implement is inserted into the user's mouth and the user bites down on the assistance implement a tube is formed between the forward region of the oral cavity insertion elastic body and the lip clamping elastic body, the assistance implement has a protruding portion provided below a transverse center of the oral cavity insertion elastic body that extends longitudinally from a front end of the oral cavity insertion elastic body to a back end of the oral cavity insertion elastic body, and the protruding portion is made of a material harder than the oral cavity insertion elastic body.

2. The assistance implement of claim 1, wherein the oral cavity insertion elastic body includes a projecting portion provided to an upper transverse center of the oral cavity insertion elastic body that is configured to make contact with the roof of the user's mouth, in the vicinity of the user's soft palate, when the assistance implement is inserted into the user's mouth; and/or a projection that is configured to make contact with the user's oral mucosa and tongue when the assistance implement is inserted into the user's mouth.

3. The assistance implement of claim 1 further comprising a stopper extending downward from a center back end of the protruding portion and keeping a tongue from sagging, the stopper being shaped into a substantially U-shaped groove, and having a vertical cross-section, opening backward, with respect to a longitudinal direction of the protruding portion.

4. The assistance implement of claim 3 further comprising a stopping unit including the protruding portion and the stopper, the stopping unit in a first embodiment being integrally formed with the assistance implement of claim 1, the stopping unit in a second embodiment having a top face of the protruding portion of the stopping unit and a bottom face of the oral cavity insertion elastic body of the assistance implement of claim 1 joined and secured together, or the stopping unit in a third embodiment having the protruding portion of the stopping unit inserted into and secured to: the oral cavity insertion elastic body formed with a stopping unit insertion belt provided below the oral cavity insertion elastic body of claim 1; and the tube including the stopping unit insertion belt.

5. The assistance implement of claim 3, wherein the stopper includes a through hole provided to an outer periphery wall of the stopper.

6. The assistance implement of claim 3, wherein the stopper has a lower portion a surface of which is coated with a coating film.

7. An assistance implement for ameliorating sleep apnea syndrome, made of an elastic body and configured to be inserted into the mouth of a human user, the assistance implement comprising:

an oral cavity insertion elastic body that is formed as a plate of material, the oral cavity insertion elastic body 1) arching upwardly as seen end-on from the front or the rear of the assistance implement, thereby leaving a cavity along an underside of the oral cavity insertion elastic body, and 2) being wide enough at a rear portion thereof for the user to be able to bite down on laterally outer edge portions of the oral cavity insertion elastic body to hold the assistance implement with the user's molars when the assistance implement is inserted into the user's mouth; and a lip clamping elastic body extending laterally from one side of the oral cavity insertion elastic body to an opposite side of the oral cavity insertion elastic body at the underside thereof such that a tube for passage of air is formed between the lip clamping elastic body and the oral cavity insertion elastic body, the tube being long enough to permit the tube to be held between the user's lips with the lip clamping elastic body abutting the user's lower anterior teeth and the tube extending forwardly past the user's lips when the assistance implement is inserted into the user's mouth;

wherein the oral cavity insertion elastic body is configured such that when the assistance implement is inserted into the user's mouth and the laterally outer edge portions of the oral cavity insertion elastic body are held between the user's molars, 1) the user's tongue will be located within the cavity along the underside of the oral cavity insertion elastic body and a space will remain between the oral cavity insertion elastic body and the roof of the user's mouth, and 2) the laterally outer edge portions will extend outwardly past the buccal sides of the user's molars and engage the user's cheeks to cause the user's cheeks to bulge outwardly.

8. The assistance implement of claim 7, wherein the rear portion of the oral cavity insertion elastic body has a double-lobed shape with rounded peripheral edges, thereby giving the rear portion of the oral cavity insertion elastic body a heart-shape configuration.

* * * * *